(12) United States Patent
Hughes et al.

(10) Patent No.: US 8,648,200 B2
(45) Date of Patent: Feb. 11, 2014

(54) IMIDAZOLE DERIVATIVES USEFUL FOR THE TREATMENT OF ARTHRITIS

(75) Inventors: Norman Earle Hughes, Indianapolis, IN (US); Bryan Hurst Norman, Indianapolis, IN (US); Timothy Andrew Woods, Edinburgh, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/468,122

(22) Filed: May 10, 2012

(65) Prior Publication Data

US 2012/0302608 A1 Nov. 29, 2012

Related U.S. Application Data

(60) Provisional application No. 61/490,222, filed on May 26, 2011.

(51) Int. Cl.
*C07D 401/00* (2006.01)
*A61K 31/44* (2006.01)

(52) U.S. Cl.
USPC ..................... 546/272.7; 514/341

(58) Field of Classification Search
None
See application file for complete search history.

(56) References Cited

U.S. PATENT DOCUMENTS

| 7,439,360 B2* | 10/2008 | Gore et al. ............... 544/364 |
| 8,084,466 B2* | 12/2011 | Kindrachuk et al. ......... 514/319 |
| 8,252,831 B2* | 8/2012 | Kuklish et al. ............. 514/398 |
| 2010/0324086 A1 | 12/2010 | Wannberg et al. | |

FOREIGN PATENT DOCUMENTS

| WO | 2009103778 | 8/2009 |
| WO | 2010100249 | 9/2010 |
| WO | 2010127152 A2 | 11/2010 |
| WO | 2011048004 | 4/2011 |

OTHER PUBLICATIONS

Brittain, H., ed., Polymorphism in Pharmaceutical Solids, 2009 excerpt pp. 318-335.*
Ivanisevic, I., Pharm. Form. Qual. 2011, pp. 30-33.*
Silverman, R. "The Organic Chemistry of Drug Design and Drug Action," 2004, Elsevier, pp. 29-32.*
Cote, et al., Substituted phenanthrene imidazoles as potent, selective, and orally active MPGES-1 inhibitors, Bioorganic & Medicinal Chemistry Letters, vol. 17, No. 24, pp. 6816-6820, 2007.
Wang, et al., "Microsomal prostaglandin E synthase-1 inhibition in cardiovascular inflammatory disease," Journal of Internal Medicine, vol. 263, pp. 500-505 (2008).
Iyer, et al., "Prostaglandin E2 synthase inhibition as a therapeutic target," Expert Opinion Therapeutic Targets, vol. 13, No. 7, pp. 849-865.
Trebino, et al., "Impaired inflammatory and pain responses in mice lacking an inducible prostaglandin E synthase," PNAS, vol. 100, No. 15, pp. 9044-9049 (2003).
Samuelsson, et al., "Membrane prostaglandin E synthase-1: a novel therapeutic target," Pharmacological Reviews, vol. 59, No. 3, pp. 207-224 (2007).
Huntjens, et al. "Pharmacokinetic-pharmacodynamic correlations and biomarkers in the development of COX-2 inhibitors," Rheumatology, vol. 44, pp. 846-859 (2005).
Breimer, et al., "Relevance of the application of pharmacokinetic-pharmacodynamic modelling concepts in drug development," Clin. Pharmacokinet, vol. 32, No. 4, pp. 259-267 (1997).
Warner, et al., "Nonsteroid drug selectivities for cyclo-oxygenase-1 rather than cyclo-oxygenase-2 are associated with human gastrointestinal toxicity: a full in vitro analysis," Proc. Natl. Acad. Sci. USA, vol. 96, pp. 7563-7568, (1999).
Werner, et al., "Investigation of the pharmacokinetics of celecoxib by liquid chromatograpy-mass spectromettry," Biomedical Chromatography, vol. 16, pp. 56-60 (2002).

* cited by examiner

*Primary Examiner* — Janet L Andres
*Assistant Examiner* — Heidi Reese
(74) *Attorney, Agent, or Firm* — James B. Myers

(57) ABSTRACT

The present invention provides compounds of the formula below:

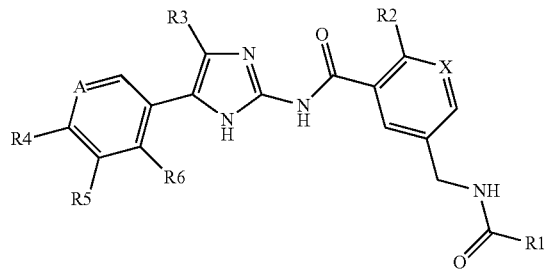

where A, X and R1-R6 are as described herein, a pharmaceutical salt thereof, and a pharmaceutical composition containing this compound; methods of treating pain associated with osteoarthritis using one of the compounds or a pharmaceutically acceptable salt thereof, and processes for preparing the compounds.

22 Claims, 1 Drawing Sheet

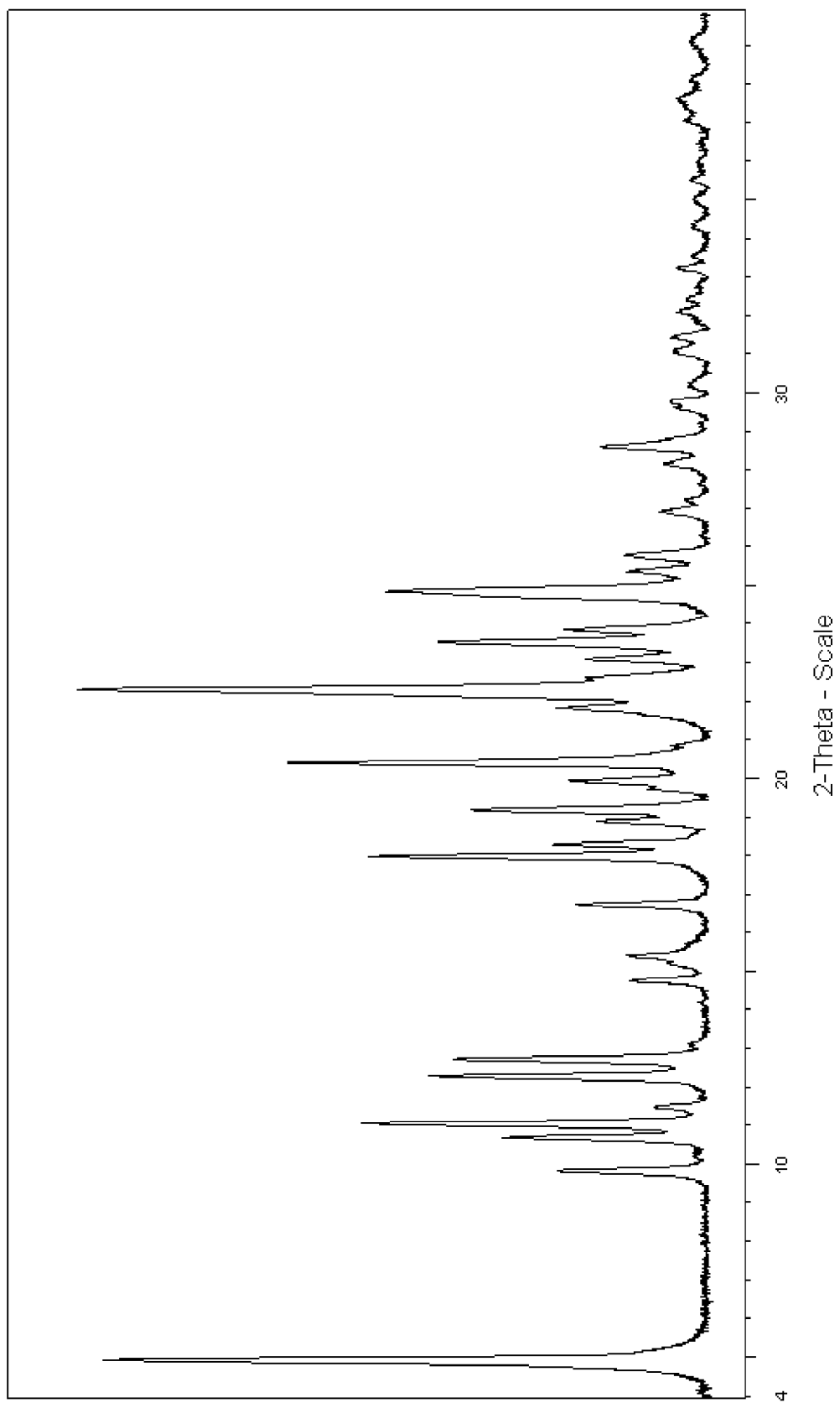

IMIDAZOLE DERIVATIVES USEFUL FOR THE TREATMENT OF ARTHRITIS

Osteoarthritis is a complex degenerative disease of joints characterized by progressive destruction of articular cartilage; peri-articular structures including bones, synovium, and associated fibrous joint tissues; and varying degrees of inflammation. Existing drug therapies can reduce pain associated with osteoarthritis, but may be only moderately effective over time and each has variable risk/benefit considerations. Current treatments using non-steroidal, anti-inflammatory drugs (NSAIDs) and Cyclooxygenase-2 inhibitors (COX-2 inhibitors) are efficacious, but can cause significant cardiovascular and gastrointestinal untoward effects. Consequently these classes of drugs may be contraindicated for many patients due to pre-existing or emergent cardiovascular and/or gastric intestinal conditions. Additionally, individuals can become refractory over time to specific drug treatments.

Prostaglandin $E_2$ is produced through the metabolism of arachidonic acid by the cyclooxygenases to generate the unstable intermediate prostaglandin $H_2$ ($PGH_2$). Prostaglandin $H_2$ is then further metabolized by microsomal prostaglandin $E_2$ synthase-1 (mPGES-1) to $PGE_2$. Prostaglandin $E_2$ is an important mediator of conditions associated with osteoarthritis, for example, fever, pain, and inflammation.

There remains a need for additional options to treat and alleviate pain and/or inflammation associated with osteoarthritis. The present invention provides novel inhibitors of mPGEs-1 and may be beneficial for treating patients suffering from the pain and/or inflammation of osteoarthritis.

The present invention provides compounds of formula I:

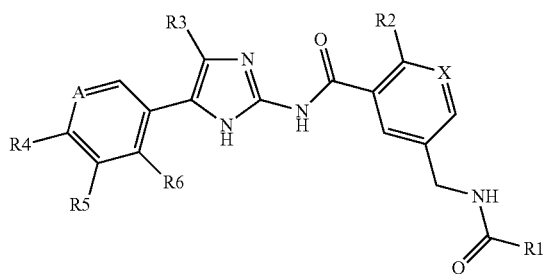

I wherein R1 is selected from: —$C_{1-4}$alkyl; R2 is Cl or —$CHF_2$; R3 is H or —$CH_3$; R4 is selected from: H, F, Cl, —$CH_3$, —$CHF_2$, and —$CF_3$; R5 is selected from: H, F, Cl, and —$CH_3$; and R6 is selected from: H, F, Cl, and —$CH_3$; and one of X and A is N and the other one of X and A is CH; provided that when A is N, R4 is not F or Cl and when X is N, R2 is not Cl; or a pharmaceutically acceptable salt thereof.

The present invention provides compounds according to formula I or pharmaceutically acceptable salts thereof, wherein R1 is selected from —$CH(CH_3)_2$ or —$C(CH_3)_3$; more preferably R1 is —$CH(CH_3)_2$.

The present invention provides compounds according to formula I or pharmaceutically acceptable salts thereof, wherein R3 is —$CH_3$.

The present invention provides compounds according to formula I or pharmaceutically acceptable salts thereof, wherein R5 is selected from: H, F, Cl. Preferably R5 is H.

The present invention provides compounds according to formula I or pharmaceutically acceptable salts thereof, wherein R6 is H.

The present invention provides compounds according to formula I or pharmaceutically acceptable salts thereof, wherein R4 is selected from: H, —$CH_3$, —$CHF_2$, and —$CF_3$. In one embodiment, A is N and X is CH.

The present invention provides compounds according to formula I or pharmaceutically acceptable salts thereof, wherein R4 is selected from: F, Cl, —$CHF_2$, and —$CF_3$. More preferably R4 is selected from: Cl, —$CHF_2$, and —$CF_3$. Still more preferably R4 is $CF_3$. In one embodiment, A is CH and X is N.

The present invention provides compounds according to formula I or pharmaceutically acceptable salts thereof, wherein R2 is Cl.

In one embodiment, A is N and X is CH. In another embodiment, A is CH and X is N.

The present invention provides compounds according to formula I or pharmaceutically acceptable salts thereof, wherein R1 is —$CH(CH_3)_2$ or —$C(CH_3)_3$; R2 is Cl or —$CHF_2$; R3 is —$CH_3$; R4 is selected from: F, Cl, —$CH_3$, —$CHF_2$, and —$CF_3$; R5 is selected from: H, F, Cl, and —$CH_3$; R6 is selected from: H, F, Cl, and —$CH_3$; one of X and A is N and the other one of X and A is CH, provided that when A is N, R4 is not F or Cl and when X is N, R2 is not Cl.

The present invention provides compounds according to formula I or pharmaceutically acceptable salts thereof, wherein R1 is —$CH(CH_3)_2$; R2 is Cl or —$CHF_2$; R3 is H or —$CH_3$; R4 is selected from: F, Cl, —$CH_3$, —$CHF_2$, and —$CF_3$; R5 is selected from: H, F, Cl, and —$CH_3$; R6 is H; one of X and A is N and the other one of X and A is CH, provided that when A is N, R4 is not F or Cl and when X is N, R2 is not Cl.

The present invention provides compounds according to formula I or pharmaceutically acceptable salts thereof, wherein R1 is —$CH(CH_3)_2$; R2 is —$CHF_2$; R3 is H or —$CH_3$; R4 is selected from: F, Cl, —$CH_3$, —$CHF_2$, and —$CF_3$; R5 is selected from: H, F, Cl, and —$CH_3$; R6 is H; one of X and A is N and the other one of X and A is CH, provided that when A is N, R4 is not F or Cl and when X is N, R2 is not Cl.

The present invention provides compounds according to formula I or pharmaceutically acceptable salts thereof, wherein R1 is —$C(CH_3)_3$; R2 is Cl or —$CHF_2$; R3 is —$CH_3$; R4 is selected from: H, F, Cl, —$CH_3$, and —$CF_3$; R5 is selected from: H, F, Cl, —$CH_3$; R6 is selected from: H, F, Cl, and —$CH_3$; one of X and A is N and the other one of X and A is CH; provided that when A is N, R4 is not F or Cl and when X is N, R2 is not Cl.

The present invention provides compounds according to formula I, and pharmaceutically acceptable salts thereof, wherein R1 is —$CH(CH_3)$ or —$C(CH_3)_3$; R2 is —$CHF_2$; R3 is H or —$CH_3$; R4 is selected from: H, F, Cl, —$CH_3$, —$CF_3$; R5 is selected from: H, F, Cl, —$CH_3$, and —$CF_3$; R6 is selected from: H, F, Cl, —$CH_3$; and one of X and A is N and the other one of X and A is CH; provided that when A is N, R4 is not F or Cl.

The present invention provides compounds according to formula I or pharmaceutically acceptable salts thereof, wherein R1 is selected from —$CH(CH_3)_2$ or —$C(CH_3)_3$; R2 is Cl or —$CHF_2$; R3 is H or —$CH_3$; R4 is selected from: H, —$CH_3$, —$CHF_2$, and —$CF_3$; R5 is H; R6 is selected from: H, F, —$CH_3$; and one of X and A is N and the other one of X and A is CH; provided that when X is N, R2 is not Cl. In one embodiment, X is CH and A is N.

The present invention provides compounds according to formula I or pharmaceutically acceptable salts thereof, wherein R1 is selected from —$CH(CH_3)_2$ or —$C(CH_3)_3$; R2 is Cl or —$CHF_2$; R3 is —$CH_3$; R4 is selected from: H, F, Cl, —CH₃, —CHF₂, and —CF₃; R5 is selected from: H, F, Cl, —CH₃, R6 is selected from; H, F, Cl, —CH₃, and one of X and A is N and the other one of X and A is CH; provided that when X is N, R2 is not Cl, and when A is N, R4 is not F or Cl. In one embodiment, X is N and A is CH.

The present invention provides compounds according to formula I or pharmaceutically acceptable salts thereof, wherein R1 is selected from —CH(CH₃)₂ or —C(CH₃)₃; R2 is Cl or —CHF₂; R3 is H or —CH₃; R4 is selected from: Cl, —CHF₂, and —CF₃, R5 is H, or Cl; R6 is H, F, —CH₃; and one of X and A is N and the other one of X and A is CH; provided that when A is N, R4 is not F or Cl and when X is N, R2 is not Cl.

The present invention provides compounds according to formula I or pharmaceutically acceptable salts thereof, R1 is selected from —CH(CH₃)₂ or —C(CH₃)₃; R2 is Cl or —CHF₂; R3 is H; or —CH₃; R4 is CF₃, R5 is H; R6 is selected from: H, F, and —CH₃; and one of X and A is N and the other one of X and A is —CH; provided that when A is N, R4 is not F or Cl and when X is N, R2 is not Cl.

The present invention provides compounds of formula I or pharmaceutically acceptable salts thereof, wherein A is N provided R4 is not F or Cl.

The present invention provides according to formula I or pharmaceutically acceptable salts thereof wherein X is N provided that R2 is not Cl.

The present invention provides compounds of formula I, and pharmaceutically acceptable salts thereof, wherein R1 is selected from —CH(CH₃) or —C(CH₃)₃; R2 is Cl; R3 is —CH₃ R4 is H; R5 is H; R6 is H; X is CH and A is N.

The present invention provides a compound which is of formula II:

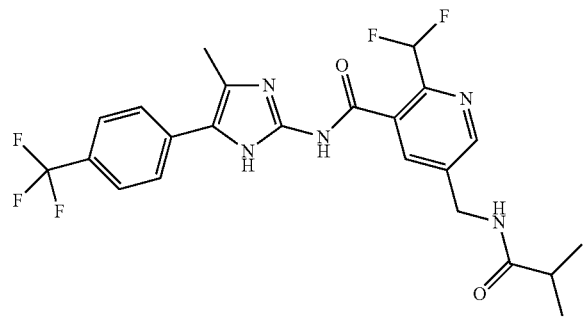 [SMILES: Cc1nc(NC(=O)c2cc(CNC(=O)C(C)C)cnc2C(F)F)[nH]c1-c1ccc(C(F)(F)F)cc1]

II or a pharmaceutically acceptable salt thereof. A preferred acid addition salt of the compounds of the invention is the hydrogen phosphate addition salt.

The present invention also provides 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen.phosphate salt in crystalline form characterized by an X-ray powder diffraction pattern obtained from a CuKα source (λ=1.54056 Å), which comprises peaks at a) 4.85°, 20.37°, and 22.27°+/−0.2° in 2θ; or b) 4.85°, 11.00°, 17.93°, 20.37°, 22.27°, and 24.85°+/−0.2° in 2θ; or c) 4.85°, 11.00°, 12.22°, 12.67°, 17.93°, 20.37°, 22.27°, 23.51°, and 24.85°+/−0.2° in 2θ; or d) 4.85°, 9.77°, 16.68°, 17.93°, 19.15°, 22.27° and 24.84°+/−0.2°.

The present invention also provides a composition comprising substantially pure 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt in crystalline form. As used herein "substantially pure" refers to a composition with greater than 80% w/w of the crystalline material, more preferably greater than 95% w/w of the crystalline material, and still yet more preferably greater than 98% w/w of the crystalline 2-(Difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt.

The present invention also provides a pharmaceutical composition comprising a compound according to formula I or II and pharmaceutically acceptable salts thereof and at least one of a pharmaceutically acceptable carrier, diluent or excipient.

The present invention provides a pharmaceutical composition comprising a compound according to formula I or and pharmaceutically acceptable salts thereof, and at least one of a pharmaceutically acceptable carrier, diluent, or excipient and further comprising one or more additional therapeutic agents.

The present invention provides a method of treating a mammal for pain and/or inflammation associated osteoarthritis; still more preferably a method of treating pain and/or inflammation associated with osteoarthritis. The method comprises administering to a mammal in need thereof a compound according to formula I or II, a pharmaceutically acceptable salt thereof, or pharmaceutically acceptable composition including the compound.

The present invention provides use of a compound according to formula I or II, or a pharmaceutically acceptable salt thereof, in the manufacture of a medicament for treating pain and/or inflammation associated with osteoarthritis.

The present invention provides a compound according to formula I or II, a pharmaceutically acceptable salt thereof, or pharmaceutical composition including the compound for use as a medicament.

The present invention provides a compound according to formula I or II, a pharmaceutically acceptable salt thereof, or a pharmaceutical composition including the compound for use in therapy.

The present invention also provides a compound according to formula I or II, a pharmaceutically acceptable salt thereof, or pharmaceutical composition including the compound for use in the treatment of pain and/or inflammation associated with osteoarthritis in a mammal in need of treatment thereof; still yet more preferable the present invention provides a method of treating pain associated with osteoarthritis in a mammal in need thereof.

FIG. 1 is a spectrogram of a representative XRD pattern for -(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen.phosphate salt. The XRD spectrogram is obtained as described in the Example 26 below.

The phrase "pharmaceutically-acceptable salt" refers to salts of the compounds of the invention considered to be acceptable for clinical and/or veterinary use. Pharmaceutically acceptable salts and common methodology for preparing the salts are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977. In one embodiment, a hydrogen phosphate addition salt is a preferred salt form.

A compound of the present invention can be combined with other treatment methods and/or additional therapeutic agents, preferably agents for the treatment of arthritis, including the pain and inflammation associated with osteoarthritis. Examples include NSAIDs or COX-2 inhibitors such as ibuprofen, aspirin, acetaminophen, celecoxib, naproxen, and ketoprofen; opiods such as oxycodone, and fentanyl; and corticosteroids such as hydrocortisone, prednisolone, and prednisone.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of formula I and II, or salts thereof. The products of each step in the schemes below can be recovered by conventional methods, including extraction, evaporation, precipitation, chromatography, filtration, trituration, and crystallization.

Additionally, the intermediates described in the following Schemes contain a number of protecting groups. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*.

The abbreviations used herein are defined according to *Aldrichimica Acta*, Vol. 17, No. 1, 1984. Other abbreviations are defined as follows: "ACN" refers to acetonitrile; "Boc$_2$O" refers to di-tert-butyl dicarbonate; "BOP" refers to benzotriazol-1-yloxy-tris(dimethylamino)-phosphonium hexafluorophosphate; "DCM" refers to dichloromethane; "DIPEA" refers to diisopropylethylamine; "DMF" refers to N,N-dimethylformamide; "DMSO" refers to dimethylsulfoxide; "EDCI" refers to N-ethyl, N'-(dimethylamino)propyl carbodiimide hydrochloride; "EDTA" refers to ethylenediaminetetraacetic acid; "Et$_2$O" refers to diethyl ether; "EtOAc" refers to ethyl acetate; "EtOH" refers to ethyl alcohol or ethanol; h refers to hour(s); "HATU" refers to 2-(1H-7-azabenzotriazol-1-yl)--1,1,3,3-tetramethyl uronium hexafluorophosphate methanaminium; "HOBT" refers to 1-hydroxylbenzotriazole hydrate; "iPr" refers to isopropyl alcohol or isopropanol; "IC$_{50}$" refers to the concentration of an agent that produces 50% of the maximal inhibitory response possible for that agent; "MeOH" refers to methyl alcohol or methanol; "MTBE" refers to methyl tert-butyl ether; "RT refers to room temperature; "T3P®" refers to propylphosphonic anhydride; and "TBTU" refers to o-benzotriazol-1-yl-N,N,N'N'-tetramethyluronium tetrafluoroborate; "THF" refers to tetrahydrofuran.

In the Schemes below, all substituents unless otherwise indicated, are as previously defined. The reagents and starting materials are generally readily available to one of ordinary skill in the art. Others may be made by standard techniques of organic and heterocyclic chemistry, which are analogous to the syntheses of known structurally-similar compounds and the procedures described in the Preparations and the Examples, which follow including any novel procedures. The compounds of the present invention can be prepared as generally illustrated below in Schemes below.

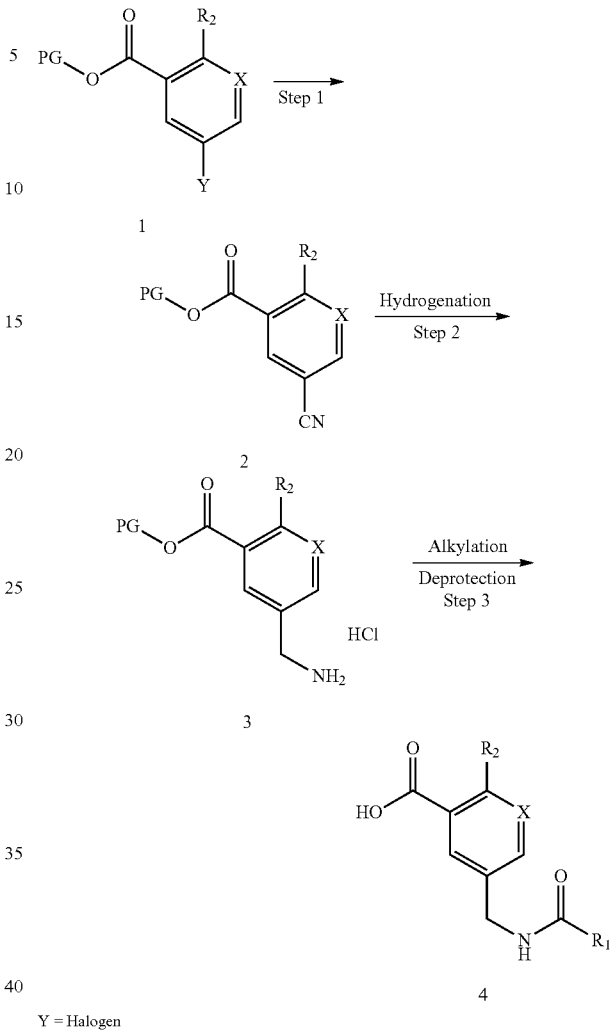

Y = Halogen

Scheme 1 illustrates the preparation of compound 4, the aryl or heteroaryl substituted 3-carboxylic acid to couple with compound 8 in Scheme 2 to prepare compounds of formula I, II or Ia.

Scheme 1 depicts the conversion of the substituted-4-aryl halogen or substituted-4-heteroaryl halogen to a cyano group, (2, Step 1) followed by the reduction of the cyano group with hydrogen to give the amine (3, Step 2) which is alkylated and deprotected to give the amide compound 4, Step 3. The "PG" group is an ester protecting group developed for acyl groups such as a methyl, ethyl or t-butyl groups. Such protecting groups are well known and appreciated in the art.

For example, the skilled artisan will recognize that there are a variety of conditions useful for selectively introducing a cyano group such as a palladium catalyzed cyanation of haloarenes. A cyanide source such as Zn(CN)$_2$, K$_4$[Fe(CN)$_6$], (CH$_3$)$_3$SiCN, NaCN, or KCN and a palladium catalyst such as tetrakis(triphenylphosphino)palladium or tris(dibenzylideneacetone)dipalladium (0) in a polar aprotic solvent such as DMF, ACN, or THF give compound 2, Step 1. Reduction of the benzonitrile to the benzylamine can be accomplished by hydrogenation with a palladium source such as 5% palladium on carbon, under acidic conditions using an acid such as hydrochloric acid under about 60 psi of hydrogen to give compound 3 in Step 2. An intermediate product of (Step 3) can be prepared using an acid chloride and an organic base such as diisopropylethylamine or triethylamine to give the amide. Deprotection of the ester under basic conditions using an aqueous base such as lithium hydroxide gives the amide (4).

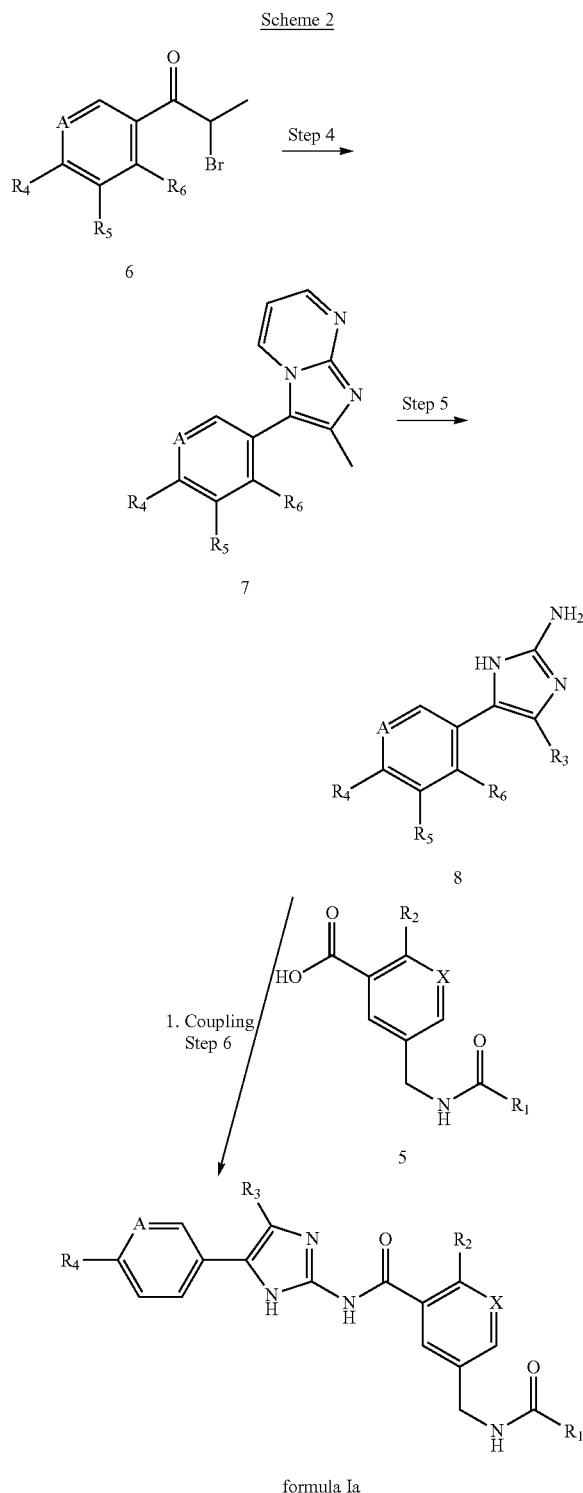

Scheme 2

Scheme 2 illustrates the preparation of a substituted aryl or substituted heteroaryl imidazole pyrimidine that is used to prepare a substituted aryl or substituted heteroaryl imidazole amine that is coupled with the aryl or heteroaryl substituted 3-carboxylic acid from Scheme 1 to give compounds of formula Ia.

For example, an imidazopyrimidine (7, Step 4) can be prepared from an appropriate α-bromo or α-chloro ketone with 2-aminopyrimidine in a polar protic solvent such as isopropanol or ethanol or a non-polar solvent such as toluene with or without a base such as sodium bicarbonate to give an imidazo[1,2-a]pyrimidine (7). The imidazo[1,2-a]pyrimidine (7) can be converted to the desired imidazol-2-amine (8, Step 5) with hydrazine, hydrazine hydrate, or hydrazine hydrochloride or hydroxylamine. The primary amino group of compound 8 can then be coupled with the carboxylic acid of compound 5 in Scheme 1 using coupling agents to give compounds of Formula Ia, I and II. Common coupling conditions involve using a coupling agent such as benzotriazol-1-yloxy-tris(dimethylamino)-phosphonium hexafluorophosphate, propylphosphonic anhydride, dicylohexylcarbodiimide, o-benzotriazol-1-yl-N,N,N'N'-tetramethyluronium tetrafluoroborate, and 2-(1H-7-azabenzotriazol-1-yl)--1,1,3,3-tetramethyl uronium hexafluorophosphate methanaminium and an organic base such as N-methylmorpholine or diisopropylamine to give compounds of formula Ia.

Unless noted to the contrary, the compounds illustrated herein are named and numbered using Symyx® Draw version 3.2 (Symyx Solutions, Inc.) or IUPACNAME ACDLABS.

PREPARATION 1

Ethyl 4,4-difluoro-3-oxo-butanoate

Add sodium metal (7 kg, 300 mol) in portions to EtOH (53.6 kg) while maintaining the temperature below 60° C. Stir the reaction mixture until the sodium dissolves, then cool the mixture to 20-30° C. Add a solution of ethyl difluoroacetate (34 kg, 274 mol) in EtOAc (63 kg) to the sodium ethoxide at a temperature of 25-40° C. Heat the reaction mixture to 65° C. while stirring. After 2 h cool the mixture to room temperature. Add 10% HCl (30 kg HCl and 204 kg water) to the mixture until the pH of the mixture is 6-7. Extract the mixture with EtOAc (64 kg); separate; and extract the aqueous layer again with EtOAc (60 kg). Combine organic phases, and wash with brine (NaCl (48 kg) in water (136 kg)). Dry the organic phase with 4 A molecular sieve powder (15 kg), and concentrate to give the title compound as a brown-yellow oil (33 kg, 73% yield, 96% GC purity). $^1$H NMR (500 MHz, CDCl$_3$,) δ 5.91 (t, J=54 Hz, 1H), 4.23 (m, 2H), 3.70 (s, 2H), 1.27 (m, 3H).

PREPARATION 2

Ethyl (2Z)-2-(ethoxymethylene)-4,4-difluoro-3-oxo-butanoate

Add acetic anhydride (166 kg, 1625 mol) to a mixture of ethyl 4,4-difluoroacetoacetate (33 kg, 199 mol) and triethyl orthoformate (60 kg, 407 mol) maintained at 90-100° C. Stir the mixture at 90-100° C. for 8.5 hours and remove ethyl acetate using a Dean-Stark apparatus. Concentrate the reaction mixture to give the title compound (37.8 kg, 86% yield, 97% GC purity). $^1$H NMR (500 MHz, CDCl$_3$,) δ 7.88 (d, J=6 Hz, 1H), 6.3 (m, 1H), 4.3 (m, 4H), 1.4 (m, 3H), 1.32 (m, 3H).

PREPARATION 3

3-Dimethylaminoprop-2-enenitrile

Add dimethyl acetal (49 kg, 412 mol) in 1,4-dioxane (30 kg) to a solution of cyanoacetic acid (30 kg, 353 mol) in 1,4-dioxane (120 kg) maintained at 80° C. Stir the resulting mixture for 4 hours. Thereafter concentrate the mixture. Dilute the residue with MTBE (44 kg); filter through a pad of silica gel; and wash the silica gel pad with MTBE (112 kg). Collect the filtrate, and concentrate under vacuum to give 48 kg crude product in solution (19.6 kg, 57% yield). $^1$H NMR (500 MHz, CDCl$_3$,) δ 6.91 (d, J=13.5 Hz, 1H), 3.7 (d, J=13.5 Hz, 1H), 2.86 (s, 6H).

PREPARATION 4

Ethyl 5-bromo-2-formylpyridine-3-carboxylate

To each of 106 separate 20-mL microwave vials, add: ethyl 5-bromo-2-methylpyridine-3-carboxylate (5 g, 20.48 mmol, 1.0 equiv), selenium dioxide (2.98 g, 26.63 mmol, 1.3 equiv), and 1,4-dioxane (13 mL). Heat the vessels to 180° C. for 20 min with microwave irradiation. Combine the contents of the reaction vessels; filter through a pad of silica gel (2 kg); and rinse the pad with DCM (3 L). Concentrate the combined filtrates under reduced pressure. Split the material into two equally-sized batches, and pass each through a pad of silica gel (2 kg) eluting with DCM. Concentrate the filtrate under reduced pressure to furnish the title compound as a yellow or pale orange solid (473 g, 93.2% yield). MS (m/z) ($^{79}$Br/$^{81}$Br) 258/260 (M+1).

PREPARATION 5

Ethyl 5-bromo-2-(difluoromethyl)pyridine-3-carboxylate

Under a nitrogen atmosphere, cool a mixture of ethyl 5-bromo-2-formylpyridine-3-carboxylate (473 g, 1.83 mol, 1.0 equiv) and DCM (4.73 L) to 0-5° C. Over a 2 h period, add a solution of diethylaminosulfur trifluoride (364 mL, 2.75 mol, 1.5 equiv) in anhydrous DCM (473 mL). Allow the mixture to warm to room temperature, and stir for 16 h. Over a 3 h period, transfer the reaction mixture in aliquots to a stirring mixture of ice (2.5 L), water (2.5 L), and NaOH (50 wt % aqueous, 400 mL), taking care to control the fuming Dilute the resulting mixture with DCM (1 L) and water (1 L). Separate the layers, and extract the aqueous layer with DCM (2.5 L). Wash the organic layer with water (2.5 L), and allow the mixture to settle for 10 minutes. Separate the layers; dry the combined organic layers over MgSO$_4$; remove the solids by filtration; and concentrate the filtrate under reduced pressure. Dissolve the resulting material in DCM (600 mL), and pass through a pad of silica gel (2 kg) eluting with DCM (20 L). Concentrate the eluent under reduced pressure, and recrystallize the resulting material from hot iso-hexanes (1 L). Allow the mixture to cool to room temperature; collect the solids by filtration; wash the solids with cold iso-hexanes; and dry under reduced pressure at 40° C. to give the title compound as an off-white crystalline powder (367 g). Combine all iso-hexanes filtrates, and cool to −20° C. Collect the resulting orange solids as a second crop of the title compound (37.5 g, combined yield 79%). MS (m/z) ($^{79}$Br/$^{81}$Br) 280/282 (M+1).

PREPARATION 6

Ethyl 5-cyano-2-(difluoromethyl)pyridine-3-carboxylate

In a flask, dissolve ethyl 5-bromo-2-(difluoromethyl)pyridine-3-carboxylate (150 g, 536 mmol, 1.0 equiv) in DMF (1.5 L). Degas the resulting mixture by evacuating then backfilling the flask with nitrogen three times. Add zinc(II) cyanide (51 g, 434 mmol, 0.81 equiv), followed by tetrakis(triphenylphosphino)palladium (25.2 g, 21.8 mmol, 0.04 equiv). Heat the resulting suspension to an internal temperature of 100° C. for 3 h. Cool the mixture to room temperature; dilute with water (2 L); and extract with diethyl ether (3×2.5 L). Wash the combined organic phases with brine (3×2.5 L). Extract the combined aqueous phases with Et$_2$O (2.5 L). Combine all organic phases, and dry over MgSO$_4$. Remove the solids by filtration, and concentrate the filtrate under reduced pressure. Purify the resulting material by flash chromatography on silica gel (2 kg), eluting with a gradient of 1:1 DCM/isohexane to 100% DCM. Obtain the title compound as colorless oil, which solidifies on standing (114 g, 94.1%). MS (m/z) 227 (M+1).

Alternate Preparation 6

Heat anhydrous DMF (57 kg) to 60-65° C. and add ethyl (2Z)-2-(ethoxymethylene)-4,4-difluoro-3-oxo-butanoate (30 kg, 135 mol) followed by the drop wise addition of a solution of 3-dimethylaminoprop-2-enenitrile (31.6 kg, 135.1 mol). Stir the resulting mixture at 60-65° C. for about 5 h. Add ammonium acetate (16 kg, 202 mol), and stir the mixture at 60-65° C. for 12 hours. Cool the reaction mixture to RT; quench with water (270 kg); extract with MTBE (114 kg); and separate the layers. Re-extract the aqueous phase with MTBE (228 kg). Combine the organic phases; wash with water (300 kg); filter through silica gel (15 kg); wash the silica gel with MTBE (114 kg); collect the filtrates; and concentrate to give the crude product (26 kg), which is purified by re-crystallization with EtOH (47.7 kg) to give the title compound (26 kg, 85% yield 98.6% purity by GC). $^1$H NMR (500 MHz, CDCl$_3$,) δ 9.09 (s, 1H), 8.61 (s, 1H), 7.44 (t, J=54 Hz, 1H), 4.49 (q, J=7 Hz, 2H), 1.46 (t, J=7 Hz, 3H).

PREPARATION 7

Ethyl 5-(aminomethyl)-2-(difluoromethyl)pyridine-3-carboxylate hydrochloride

Purge a mixture of methyl 5-cyano-2-(difluoromethyl)pyridine-3-carboxylate (160 g, 707.4 mmol) and EtOH (2 L) with nitrogen and stir 15 min. Add hydrochloric acid (37 wt % aqueous, 273 mL, 3183.2 mmol, 4.5 equiv) and palladium (5% on carbon, 48 g, 22.5 mmol, 0.031 equiv) in EtOH (100 mL), and stir the resulting suspension under 60 psi of hydrogen at room temperature for 70 min. Remove the solids by filtration over diatomaceous earth; wash the solid cake with EtOH (1 L); and concentrate the filtrate under reduced pressure. Repeat this procedure twice; combine the solids; and slurry in Et$_2$O:DCM [10:1, 5.5 L]. Filter the solids and dry the resulting material at 45° C. for 3 hours to give the title compound as a light brown solid (714 g, 96% yield). MS (m/z) 216 (M+1).

PREPARATION 8

Ethyl 5-(aminomethyl)-2-(difluoromethyl)pyridine-3-carboxylate dihydrochloride

Add a mixture of ethyl 5-cyano-2-(difluoromethyl)pyridine-3-carboxylate (24 kg, 122 mol), EtOH (234 kg), Et$_3$N (16 kg, 157 mol), Boc$_2$O (57 kg, 251 mol) and wet 5% Pd/C (14.2 kg, KF=50%, 0.6 g/g) to an autoclave. Stir the reaction mixture at 20-30° C. under 0.3-0.4 MPa hydrogen pressure.

Empty the autoclave, and refill with fresh hydrogen every hour for 14.5 hours. Thereafter filter the reaction mixture, and wash with EtOH (28.4 kg). Concentrate the combined filtrates to give the tert-butoxycarbonyl (BOC) protected intermediate. Dilute the material with water (70 kg), and extract with DCM (124 kg). Separate the organic layer with active carbon (1.9 kg, 0.1 g/g) and 4 Å molecular sieve powder (9.5 kg). Stir the mixture for 3 hours and then filter. Dilute the filtrate with MTBE (140 kg), and treat with HCl (19.2 kg) and 1,4-dioxane (80 kg) at 20-30° C. to give a suspension. Add a solution of water (5.0 kg) and 1,4 dioxane (15 kg) dropwise then filter the resulting mixture. Wash the resulting filter cake with MTBE (48 kg) and DCM (138 kg) to give the title product as an off-white solid (18.5 kg, 66.3%, 98% HPLC). $^1$H NMR (500 MHz, d$_6$-DMSO) δ 9.00 (s, 1H), 8.85 (s, 2H), 8.56 (s, 1H), 7.42 (t, J=54 Hz, 1H), 4.37 (q, J=7 Hz, 2H), 4.20 (q, J=7 Hz, 2H), 1.34 (t, J=7 Hz, 3H).

PREPARATION 9

Ethyl 2-(difluoromethyl)-5-{[(2-methylpropanoyl) amino]methyl}pyridine-3-carboxylate In a thermally controlled reactor stir a mixture of ethyl 5-(aminomethyl)-2-(difluoromethyl)pyridine-3-carboxylate hydrochloride (198 g, 742.4 mmol, 1.0 equiv), DCM (3040 mL), and DIPEA (520 mL, 2.98 mol, 4 equiv), then add a solution of isobutyryl chloride (95 mL, 903 mmol, 1.2 equiv) at such a rate so that the internal temperature is held between 18° C. and 22° C. Stir for 90 min. Extract the reaction mixture with NaHCO$_3$ (sat., 1 L). Add water (1 L) and DCM (1 L), and filter the resulting suspension through diatomaceous earth. Combine all organic phases, and dry over MgSO$_4$. Remove the solids by filtration, and concentrate the filtrate under reduced pressure. Purify the resulting material by slurrying with iso-hexane:Et$_2$O [1:1, 1 L]. Collect the solids by filtration, wash with cold iso-hexanes (500 ml), and dry under vacuum at 50° C. to give the title compound as an off-white crystalline powder (164 g). MS (m/z) 301 (M+1).

PREPARATION 10

2-(Difluoromethyl)-5-{[(2-methylpropanoyl)amino] methyl}pyridine-3-carboxylic acid Dissolve ethyl 2-(difluoromethyl)-5-{[(2-methylpropanoyl)amino]methyl}pyridine-3-carboxylate (414 g, 1.38 mol, 1.0 equiv) in 1,4-dioxane (4.97 L). Add water (2.48 L) and lithium hydroxide (125.6 g, 2.96 mol, 2.5 equiv); then stir the resulting mixture for 60 min at room temperature. Concentrate the 1,4-dioxane solution to ½ volume under reduced pressure, and add hydrochloric acid (5 N, 1.16 L, 5.79 mol, 4.2 equiv) slowly to maintain temperature at less than 20° C. until the pH is 2. Collect the solids by filtration; air dry for 18 hours; and then in a vacuum oven at 40° C. for 18 hours to give a white solid, (355.4 g, 94.7% yield). MS (m/z) 303 (M+1).

Alternate Preparation 10

Add ethyl 5-(aminomethyl)-2-(difluoromethyl)pyridine-3-carboxylate dihydrochloride (0.5003 kg, 1.649 mol), anhydrous toluene, (3.0277 kg), and triethylamine (0.8347 kg, 8.24 mol) to a 15-L reactor under nitrogen. Cool the reaction to 5° C. Add a solution of isobutyryl chloride (0.2110 kg, 1.98 mol) in anhydrous toluene, (0.4352 kg) drop wise over 6 min while maintaining the temperature at 0-15° C. Warm the resulting slurry to 20° C., and continue stirring for 1.25 h. Add lithium hydroxide solution (prepared by using LiOH, monohydrate (0.3561 kg) and water (2.5377 kg) to the reaction slurry over 20 minutes. Stir the mixture at 15-25° C. overnight (18.8 hours). Separate the layers, and wash the aqueous layer with anhydrous toluene (1.0796 kg). Separate the layers, and acidify the aqueous phase to pH=3.5-4.5 with 6 N HCl (0.5521 kg made from 12 N HCl and water). Stir the slurry at 15-25° C. for 1.6 hours. Isolate the solids by filtration. Rinse the reactor with the filtrate twice, and then wash the solids with water (1.0 kg) and anhydrous toluene (0.867 kg). Dry the wet solids under reduced pressure at 70° C., for 65.2 hours to give the title compound (0.3146 kg, 70% yield). $^1$H-NMR (400 MHz, d$_6$-DMSO) δ 8.72 (d, J=2.0 Hz, 1H), 8.48 (t, J=5.8 Hz, 1H), 8.17 (s, 1H), 7.51 (t, J=54.3 Hz, 1H), 4.38 (d, J=5.8 Hz, 2H), 2.45 (m, J=6.8 Hz, 1H), 1.03 (d, J=6.8 Hz, 6H)

PREPARATION 11

2-Bromo-1-(4-(trifluoromethyl)phenyl)propan-1-one

Add 4-Trifluoromethyl propiophenone (100 g, 0.494 mol) to glacial acetic acid (200 mL) at 20 to 25° C. Add bromine (79 g, 0.494 mol) in glacial acetic acid (200 mL) over 60 minutes. Stir the reaction mixture for 1 to 1.5 hours. Quench the reaction in 1.2 L of chilled water (0 to 5°) and stir the mixture for 3 hours at the same temperature. Filter the slurry; washed solids with water (1 L) at 10 to 15° C.; and dry the solids under vacuum at 25 to 30° C. for 15 hours to give the title compound (128.1 g, 92.1% yield). $^1$H NMR (300 MHz, d$_6$-DMSO) δ 8.20-8.23 (d, J=8.4 Hz, 2H), 7.80-7.93 (d, J=8.4 Hz, 2H), 5.82-5.89 (q, J=6.3 Hz, 1H), 1.79-1.81 (d, J=6.3 Hz, 3H).

PREPARATION 12

2-Methyl-3-[4-(trifluoromethyl)phenyl]imidazo[1,2-a]pyrimidine

In a thermally controlled reactor, stir a mixture of 2-bromo-1-[4-(trifluoromethyl)phenyl]propan-1-one (500 g, 1.78 mol, 1 equiv), IPA (5 L), 2-aminopyrimidine (205 g, 2.13 mol, 1.2 equiv), and sodium bicarbonate (298.8 g, 3.55 mol, 2 equiv) at 80° C. for 18 hours. Cool the suspension, and concentrate in vacuo. Dilute the resulting mixture in DCM (5 L), and wash with brine (2 L). Re-extract the brine wash with DCM (2.5 L); combine all the organic phases; and dry over MgSO$_4$; filter; and collect the filtrate. Concentrate the filtrate to dryness under reduced pressure, and slurry the resulting red gum in Et$_2$O (1.5 L). Collect the resulting solid by filtrate, and air dry for 45 min to give the title compound as a fine, off white solid (108 g, 22% yield). MS (m/z) 278 (M+1).

Alternate Procedure A

PREPARATION 12

2-Methyl-3-[4-(trifluoromethyl)phenyl]imidazo[1,2-a]pyrimidine

Dissolve 2-bromo-1-[4-(trifluoromethyl)phenyl]propan-1-one (7.120 g, 25.332 mmol) and 2-aminopyrimidine (5.464 g, 55.729 mmol) in EtOH (40.0 mL). Heat the mixture to reflux, and stir for 24 hours. Concentrate in vacuo. Dissolve the residue in EtOAc (750 mL); and wash sequentially with saturated aqueous NaS$_2$O$_3$ (250 mL), saturated aqueous NaHCO$_3$ (250 mL), and saturated NaCl (350 mL). Crystallize the orange residue from heptanes/EtOAc to give the title product as a white solid (3.29 g, 46.85% yield). $^1$H NMR (399.83 MHz, d$_6$-DMSO) δ 8.84 (dd, J=1.9, 7.0 Hz, 1H), 8.54 (dd, J=2.0, 4.2 Hz, 1H), 8.06-8.04 (m, 2H), 7.83-7.81 (m, 2H), 7.10 (dd, J=4.1, 6.9 Hz, 1H), 2.68 (s, 3H).

Alternate Procedure B Preparation 12

2-Methyl-3-[4-(trifluoromethyl)phenyl]imidazo[1,2-a]pyrimidine

Add 2-bromo-1-(4-(trifluoromethyl)phenyl)propan-1-one (100 g, 0.356 mol), 2-aminopyrimidine (33.85 g, 0.356 mol), and sodium bicarbonate (59.8 g, 0.811 mol) to toluene (500 mL) at 25 to 30° C. Heat the mixture to 90 to 100° C. and stir for 24 hours. Thereafter cool the mixture to 40 to 45° C., and distill the title compound under reduced pressure. Cool the distillate to 25 to 30° C.; add water (1 L); and stir the mixture 4 hours. Filter the mixture collecting the solid, and then wash the solid with a 10% solution of MTBE (200 mL) in hexane. Dry the solid under vacuum at 45 to 50° C. for 12 hours to give the title compound (35.4 g, 35% yield). $^1$H NMR (300 MHz, $CDCl_3$) δ 8.58 (q, 1H), 8.24-8.26 (d, J=6.6 Hz, 1H), 8.00-8.02 (d, J=8.1 Hz, 2H), 7.72-7.75 (d, J=8.4 Hz, 2H), 6.92-6.96 dd, J=3.9 Hz and 4.2 Hz, 1H), 2.69 (s, 3H).

PREPARATION 13

4-Methyl-5-[4-(trifluoromethyl)phenyl]-1H-imidazol-2-amine

Stir a mixture of 2-methyl-3-[4-(trifluoromethyl)phenyl]imidazo[1,2-a]pyrimidine (180 g, 649.2 mmol, 1 equiv) in EtOH (1.4 L) and hydroxylamine (159 ml, 2.596 mol, 4 equiv) at an internal temperature of 82° C. for 48 hours. Cool the mixture, and concentrate to dryness. Dilute the residue with DCM (1.5 L), and wash sequentially with water (2×500 ml) and brine (500 ml). Dry the organic phase over $MgSO_4$; filter; collect the filtrate and; and remove the solvent in vacuo to give a yellow gum. Purify the resulting material by flash chromatography on silica gel (2 kg), eluting with a gradient of 4:1:0.02 DCM/MeOH/$NH_3$ to obtain the title compound as a yellow foam (95% yield). MS (m/z) 242 (M+1).

Prepare the following compounds in Table 1 essentially by the method of Preparation 13 with the appropriate imidazopyrimidine.

PREPARATION 20

3-Bromo-4-(dibromomethyl)benzonitrile

Heat a mixture of 3-bromo-4-methylbenzonitrile (25.0 g, 127.5 mmol, 1.0 equiv) and n-bromosuccinimide (NBS) (5.53 g, 306.1 mmol, 2.4 equiv) in carbon tetrachloride (200 mL) to 95° C. for two days. Cool the resulting suspension, and remove the solids by filtration. Concentrate the filtrate under reduced pressure, and purify the resulting crude material by chromatography on silica gel eluting with a gradient of 2-5% THF/hexanes to furnish the title compound (37.09 g, 82% yield). $^1$H NMR (400 MHz, $CDCl_3$) δ 8.10 (d, 1H, J=8.2 Hz), 7.79 (d, 1H, J=1.3 Hz), 7.67 (dd, 1H, J=8.2, 1.3 Hz), 6.99 (s, 1H).

PREPARATION 21

3-Bromo-4-(difluoromethyl)benzonitrile

Add silver tetrafluoroborate (26.69 g, 135.7 mmol, 2.5 equiv) to a solution of 3-bromo-4-(dibromomethyl)benzonitrile (19.2 g, 54.3 mmol, 1.0 equiv) in DCM (200 mL) under a nitrogen atmosphere, and stir overnight at room temperature. Remove the solids by filtration; concentrate the filtrate under reduced pressure; and subject the resulting crude material to silica gel chromatography eluting with a gradient of 2-5% THF/hexanes to furnish the title compound (9.0 g, 71% yield). ES/MS (m/z) ($^{79}$Br/$^{81}$Br) 231/233 (M).

PREPARATION 22

Methyl 5-cyano-2-(difluoromethyl)benzoate

Purge a mixture of 3-bromo-4-(difluoromethyl)benzonitrile (8.87 g, 38.2 mmol, 1.0 equiv), triethylamine (16.0 mL, 114.7 mmol, 3.0 equiv), MeOH (70 mL), and DMF (120 mL) with nitrogen; then treat the mixture with palladium(II) acetate (867 mg, 3.82 mmol, 0.1 equiv) and 1,3-bis(diphenylphosphino)propane (1.61 g, 3.82 mmol, 0.1 equiv). Stir the mixture under 138 kPag of carbon monoxide at room

TABLE 1

| Prep. | Name | ES/MS (m/z) or $^1$H NMR |
|---|---|---|
| 14 | 5-[6-(Trifluoromethyl)-3-pyridyl]-1H-imidazol-2-amine | $^1$H NMR (399.83 MHz, $d_6$-DMSO) δ 10.68-10.66 (m, 1H), 8.96-8.96 (m, 1H), 8.14-8.11 (m, 1H), 7.73 (d, J = 8.4 Hz, 1H), 7.34-7.33 (m, 1H), 5.48-5.46 (m, 2H). |
| 15 | 4-Methyl-5-[6-(trifluoromethyl)-3-pyridyl]-1H-imidazol-2-amine | $^1$H NMR (399.83 MHz, $d_6$-DMSO) δ 8.85 (d, J = 2.2 Hz, 1H), 8.14 (s, 1H), 8.02 (dd, J = 1.8, 8.1 Hz, 1H), 7.77 (d, J = 8.1 Hz, 1H), 5.65-5.63 (m, 2H), 2.29 (s, 3H). |
| 16 | 5-[4-(Difluoromethyl)phenyl]-1H-imidazol-2-amine | $^1$H NMR (399.83 MHz, $d_6$-DMSO) δ 10.52-10.49 (m, 1H), 7.76-7.75 (m, 2H), 7.45-7.43 (m, 2H), 7.12-7.10 (m, 2H), 5.33-5.30 (m, 2H). |
| 17 | 5-[4-(Difluoromethyl)phenyl]-4-methyl-1H-imidazol-2-amine | $^1$H NMR (399.80 MHz, $d_6$-DMSO) δ 7.60-7.54 (m, 2H), 7.51-7.47 (m, 2H), 7.09-6.81 (m, 1H), 5.50-5.47 (m, 2H), 2.23 (s, 3H). LCMS: 224 (M + 1) |
| 18 | 5-(4-Fluorophenyl)-4-methyl-1H-imidazol-2-amine | $^1$H NMR (399.83 MHz, $d_6$-DMSO) δ 10.51-10.50 (m, 1H), 7.49-7.46 (m, 2H), 7.12-7.07 (m, 2H), 5.05 (s, 2H), 2.18 (s, 3H). |
| 19 | 4-Methyl-5-(p-tolyl)-1H-imidazol-2-amine | $^1$H NMR (399.83 MHz, $CDCl_3$) δ 7.59 (d, J = 2.1 Hz, 2H), 7.32 (d, J = 8.1 Hz, 2H), 7.11 (d, J = 7.9 Hz, 2H), 6.33 (t, J = 2.1 Hz, 1H), 2.22 (s, 3H). | temperature for two days and then 80° C. for one day. Cool the mixture to room temperature, and dilute with Et₂O (300 mL). Wash the mixture with water and saturated sodium chloride, and separate the organic layer. Dry the organic layer over sodium sulfate; filter; collect the filtrate; and concentrate under reduced pressure. Subject the resulting crude material to silica gel chromatography eluting with a gradient of 10-15% THF/hexanes gradient to give the title compound (6.19 g, 77% yield). ES/MS (m/z) 211 (M).

PREPARATION 23

Methyl 5-chloro-2-(trifluoromethyl)benzoate

Dissolve 5-chloro-2-(trifluoromethyl)benzoic acid (10 g, 0.044 mol) in MeOH (150 mL). Add thionyl chloride (50 g, 0.421 mol) slowly. Heat the resulting mixture to 70° C., and stir for 12 hours. Concentrate the mixture under reduced pressure. Pour the residue into water (100 mL), and extract the aqueous with EtOAc (2×200 mL). Dry the combined organics over sodium sulfate, and concentrate under reduced pressure to give the title compound (11.5 g, 96.5%) as an oil. $^1$H NMR (300 MHz, CDCl₃,) δ 7.78 (d, J=2.1 Hz, 1H), 7.69 (d, J=8.4 Hz, 1H), 7.57 (dd, J=2.1, 8.7 Hz, 1H), 3.95 (s, 3H).

PREPARATION 24

Methyl 5-cyano-2-(trifluoromethyl)benzoate

Dissolve methyl 5-chloro-2-(trifluoromethyl)benzoate (500 mg, 2.1 mmol), zinc (II) cyanide (197 mg, 1.68 mmol), zinc (55 mg, 0.84 mmol), di-palladium (II) tris(dibenzylideneacetone) (192 mg, 0.21 mmol), and diphenylphosphino ferrocene (233 mg, 0.42 mmol) in dimethylacetamide (20 mL). Heat the reaction mixture to 85° C., and stir for 12 hours. Pour the resulting mixture into water, and extract with EtOAc (2×100 mL). Dry the combined organics over sodium sulfate; filter; collect the filtrate; and concentrate the filtrate under reduced pressure. Purify the residue by silica gel chromatography eluting with 50:1 petroleum ether:EtOAc to give the title compound (320 mg, 66.5% yield) as a white solid. $^1$H NMR (300 MHz, CDCl₃,) δ 8.09 (s, 1H), 7.90 (s, 2H), 3.80 (s, 3H).

PREPARATION 25

Methyl 5-(aminomethyl)-2-(difluoromethyl)benzoate hydrochloride

Purge a mixture of methyl 5-cyano-2-(difluoromethyl) benzoate (9.37 g, 44.4 mmol, 1.0 equiv), palladium (10% on carbon, 3.00 g, 2.82 mmol, 0.064 equiv), and MeOH (50 mL) with nitrogen; then add hydrochloric acid (37 wt % aqueous, 8.0 mL, 105.6 mmol, 2.38 equiv); and stir the resulting suspension under 275 kPag of hydrogen at room temperature overnight. Remove the solids by filtration; concentrate the filtrate under reduced pressure; and dry the resulting material in a 40° C. vacuum oven overnight to give the title compound as a light brown solid (7.01 g, 83% yield). ES/MS (m/z) 216 (M+1).

PREPARATION 26

Methyl 5-(aminomethyl)-2-(trifluoromethyl)benzoate hydrochloride

Prepare essentially by the method of Preparation 25 with the appropriate nitrile. ES/MS m/z 234 (M+1-Cl).

PREPARATION 27

2-(Difluoromethyl)-5-[(2-methylpropanoylamino) methyl]benzoic acid

Add isobutyryl chloride (0.571 mL, 5.42 mmol, 1.05 equiv) to a mixture of methyl 5-(aminomethyl)-2-(difluoromethyl)benzoate hydrochloride (1.30 g, 5.17 mmol, 1.0 equiv) and triethylamine (1.51 mL, 10.85 mmol, 2.1 equiv) in DCM (50 mL) at room temperature and stir the mixture for one hour. Dilute the mixture with DCM; wash with water; then with a saturated sodium chloride aqueous solution. Separate the organic layer; dry over sodium sulfate; filter; and concentrate the filtrate under reduced pressure. Dissolve the resulting crude material in 1,4-dioxane (10 mL), and add sodium hydroxide (5 N, 2 mL, 10 mmol, 1.93 equiv). Stir the resulting suspension at 40° C. overnight. Concentrate the mixture under reduced pressure, and treat the resulting residue with 1 N aqueous hydrochloric acid until the pH reaches 3. Extract the resulting suspension with EtOAc (2×30 mL). Wash the combined organic layers with a saturated sodium chloride aqueous solution (50 mL); dry over sodium sulfate; filter; and concentrate the filtrate under reduced pressure to give the title compound as a white solid (1.32 g, 94% yield). ES/MS (m/z) 272 (M+1).

PREPARATION 28

Ethyl 2-(difluoromethyl)-5-[2-methylpropanoylamino)methyl]pyridine-3-carboxylate Treat a mixture of ethyl 5-(aminomethyl)-2-(difluoromethyl)pyridine-3-carboxylate dihydrochloride (18.9 g, 62.3 mmol, 1.0 equiv), DCM (300 mL), and N,N-diisopropylethylamine (49.4 mL, 283.5 mmol, 4.54 equiv) with isobutyryl chloride (8.95 mL, 85.05 mmol, 1.36 equiv). Stir the resulting suspension at room temperature for 90 minutes; pour the mixture into a saturated sodium bicarbonate aqueous solution (50 mL); and extract with DCM (3×20 mL). Combine the organic extracts; dry over MgSO₄; remove the solids by filtration; and concentrate the filtrate under reduced pressure to give a yellow semi-solid. Triturate the material with 1:1 Et₂O: isohexane (100 mL), and filter to isolate the title compound as a white solid (17.5 g, 93.6% yield). ES/MS (m/z) 301 (M+1).

Alternate Preparation 28

Ethyl 2-(difluoromethyl)-5-[(2-methylpropanoylamino)methyl]pyridine-3-carboxylate Cool a mixture of ethyl 5-(aminomethyl)-2-(difluoromethyl)pyridine-3-carboxylate dihydrochloride (29.8 g, 111.8 mmol, 1.0 equiv), DCM (510 mL), and triethylamine (59.2 mL, 424.6 mmol, 3.8 equiv) to 0° C., then add a solution of isobutyryl chloride (15.3 mL, 145.3 mmol, 1.3 equiv) in DCM (23 mL) drop wise over 20 min. Stir overnight while allowing the mixture to warm to room temperature. Remove the solid precipitate by filtration, and rinse the filter with EtOAc (500 mL). Concentrate the filtrate under reduced pressure; filter the concentrate to remove the solids; and rinse the solids with EtOAc. Concentrate the filtrate under reduced pressure to give a yellow oil. Subject this crude material to silica gel chromatography eluting with a gradient of 40-90% EtOAc/hexanes gradient, to give the title compound as a light yellow crystalline solid (25.8 g, 77% yield). ES/MS (m/z) 301 (M+1).

Prepare the following compounds in Table 2 essentially by the method of Preparation 28 with the appropriate ammonium salt or primary amine.

TABLE 2

| Prep. | Name | ES/MS (m/z) or $^1$H NMR |
|---|---|---|
| 29 | Methyl 5-(acetamidomethyl)-2-(difluoromethyl)benzoate | $^1$H NMR (399.80 MHz, d$_6$-DMSO) δ 8.46-8.43 (m, 1H), 7.81 (s, 1H), 7.72 (d, J = 8.2 Hz, 1H), 7.61-7.32 (m, 2H), 4.30 (d, J = 6.0 Hz, 2H), 3.84 (s, 3H), 1.85 (s, 3H). |
| 30 | Methyl 2-(difluoromethyl)-5-[(propanoylamino)methyl]benzoate | $^1$H NMR (399.80 MHz, d$_6$-DMSO) δ 8.37 (dt, J = 6.0, 5.5 Hz, 1H), 7.81 (s, 1H), 7.72 (d, J = 8.2 Hz, 1H), 7.60-7.32 (m, 2H), 4.31 (d, J = 6.0 Hz, 2H), 3.84 (s, 3H), 2.13 (q, J = 7.6 Hz, 2H), 1.00 (t, J = 7.6 Hz, 3H). |
| 31 | Methyl 2-(difluoromethyl)-5-[(2,2-dimethylpropanoylamino)methyl]benzoate | $^1$H NMR (400.13 MHz, CDCl$_3$) δ 7.91 (s, 1H), 7.78 (d, J = 8.3 Hz, 1H), 7.63-7.36 (m, 2H), 6.06 (s, 1H), 4.50 (d, J = 5.4 Hz, 2H), 3.93 (s, 3H), 1.25 (s, 10H). |
| 32 | Methyl 2-chloro-5-[(2-methylpropanoylamino)methyl]benzoate | 270/272 (M + 1 Cl$^{35}$/Cl$^{37}$) |
| 33 | Methyl 5-[(2-methylpropanoylamino)methyl]-2-(trifluoromethyl)benzoate | $^1$H NMR (399.80 MHz, d$_6$-DMSO) δ 8.20-8.17 (m, 1H), 7.80 (d, J = 8.2 Hz, 1H), 7.63 (s, 1H), 7.55 (dd, J = 0.7, 8.1 Hz, 1H), 4.32 (d, J = 6.0 Hz, 2H), 3.84 (s, 3H), 1.11 (s, 9H). |
| 34 | Ethyl 2-(difluoromethyl)-5-[(2,2-dimethylpropanoylamino)methyl]pyridine-3-carboxylate | $^1$H NMR (300.11 MHz, DMSO) δ 8.74 (d, J = 2.1 Hz, 1H), 8.27 (t, J = 5.7 Hz, 1H), 8.12 (s, 1H), 7.60-7.24 (m, 1H), 4.39-4.32 (m, 4H), 1.35-1.26 (m, 3H), 1.13 (s, 9H). |

PREPARATION 35

Ethyl 5-[(tert-butoxycarbonylamino)methyl]-2-(difluoromethyl)pyridine-3-carboxylate Combine ethyl 5-(aminomethyl)-2-(difluoromethyl)pyridine-3-carboxylate hydrochloride (17.849 mmol, 4.760 g), THF (180 mL) and tert-butoxycarbonyl tert-butyl carbonate (21.419 mmol, 4.675 mL). Stir the mixture at room temperature for about 10 minutes. Add triethylamine (5.225 mL, 37.484 mmol), and stir at room temperature 16 hours. Remove the solids by vacuum filtration, and rinse with EtOAc. Concentrate the filtrate under reduced pressure. Purify the resulting yellow oil by silica gel chromatography (220 g RediSep® silica gel column) eluting with a gradient of 5-45% EtOAc gradient in hexane to give the title compound (3.62 g, 68% yield) as a light yellow crystalline solid. $^1$H NMR (399.80 MHz, d$_6$-DMSO) δ 8.71 (d, J=2.1 Hz, 1H), 8.15-8.13 (m, 1H), 7.56-7.24 (m, 2H), 4.33 (q, J=7.1 Hz, 2H), 4.24-4.21 (m, 2H), 1.36 (s, 9H), 1.30 (t, J=7.1 Hz, 3H). LCMS (m/z) 331 (M+1).

PREPARATION 36

2-(Difluoromethyl)-5-[2-methylpropanoylamino)methyl]pyridine-3-carboxylic acid

Stir a mixture of ethyl 2-(difluoromethyl)-5-[(2-methylpropanoylamino)methyl]pyridine-3-carboxylate (19.0 g, 63.3 mmol, 1.0 equiv), 1,4-dioxane (244 mL), water (125 mL), and lithium hydroxide (5.71 g, 136 mmol, 2.15 equiv) at room temperature for 1 h. Acidify the mixture to pH=2 with aqueous hydrochloric acid (5 N, 53.1 mL, 266 mmol, 4.2 equiv). Remove the organic solvent under reduced pressure; dilute the resulting suspension with water (500 mL); and filter. Collect the resulting white solid; wash the white solid with water (2×150 mL); and air-dry for 18 h to give the title compound as a fine white solid (18.0 g, 92% yield). ES/MS (m/z) 273 (M+1).

Prepare the following compounds in Table 3 essentially by the method of Preparation 36 with the appropriate ester.

TABLE 3

| Prep. | Base | Name | ES/MS (m/z) or $^1$H NMR |
|---|---|---|---|
| 37 | LiOH | 2-(Difluoromethyl)-5-[(2,2-dimethylpropanoylamino)methyl]pyridine-3-carboxylic acid | $^1$H NMR (399.80 MHz, d$_6$-DMSO) δ 8.68 (d, J = 2.1 Hz, 1H), 8.21 (t, J = 5.9 Hz, 1H), 8.13-8.13 (m, 1H), 7.60-7.33 (m, 1H), 4.34 (d, J = 5.8 Hz, 2H), 1.10 (s, 9H). |
| 38 | LiOH | 5-[(tert-Butoxycarbonylamino)methyl]-2-(difluoromethyl)pyridine-3-carboxylic acid | $^1$H NMR (399.80 MHz, d$_6$-DMSO) δ 8.40 (d, J = 2.3 Hz, 1H), 8.12-7.84 (m, 2H), 7.50 (t, J = 6.1 Hz, 1H), 4.14-4.11 (d, J = 6.1 Hz, 2H), 1.35 (s, 9H). |

TABLE 3-continued

| Prep. | Base | Name | ES/MS (m/z) or $^1$H NMR |
|---|---|---|---|
| 39 | LiOH | 2-chloro-5-[(2-methylpropanoylamino)methyl]benzoic acid | 256 (M + 1) |
| 40 | LiOH | 5-(Acetamidomethyl)-2-(difluoromethyl)benzoic acid | $^1$H NMR (399.80 MHz, d$_6$-DMSO) δ 13.51-13.47 (m, 1H), 8.45-8.42 (m, 1H), 7.83 (s, 1H), 7.70-7.39 (m, 3H), 4.30 (d, J = 6.0 Hz, 2H), 1.85 (s, 3H). |
| 41 | LiOH | 2-(Difluoromethyl)-5-[(propanoylamino)methyl]benzoic acid | $^1$H NMR (399.80 MHz, d$_6$-DMSO) δ 13.63-13.60 (m, 1H), 8.39-8.36 (m, 1H), 7.83 (s, 1H), 7.70-7.39 (m, 3H), 4.30 (d, J = 6.1 Hz, 2H), 2.13 (q, J = 7.6 Hz, 2H), 0.99 (t, J = 7.6 Hz, 3H). |
| 42 | LiOH | 2-(Difluoromethyl)-5-[(2,2-dimethylpropanoylamino)methyl]benzoic acid | $^1$H NMR (399.80 MHz, d$_6$-DMSO) δ 13.46 (s, 1H), 8.16 (t, J = 6.0 Hz, 1H), 7.82 (s, 1H), 7.71-7.40 (m, 3H), 4.30 (d, J = 6.0 Hz, 2H), 1.11 (s, 9H). |
| 43 | sodium hydroxide | 5-[(tert-Butoxycarbonylamino)methyl]-2-(difluoromethyl)benzoic acid | 300 (M − 1) |
| 44 | sodium hydroxide | 5-[(2-Methylpropanoylamino)methyl]-2-(trifluoromethyl)benzoic acid | H1 NMR (400.43 MHz, d$_6$-DMSO) δ 13.66-13.63 (s, 1H), 8.38-8.35 (m, 1H), 7.74 (d, J = 8.1 Hz, 1H), 7.60 (s, 1H), 7.49 (dd, J = 0.8, 8.0 Hz, 1H), 4.30 (d, J = 5.9 Hz, 2H), 2.42-2.36 (septet, J = 6.8 Hz, 1H), 0.99 (d, J = 6.8 Hz, 6H). |

PREPARATION 45

5-Bromo-2-(difluoromethyl)pyridine

Dissolve 5-bromopyridine-2-carboxaldehyde (10.0 g, 53.76 mmol) in DCM (200 mL). Add bis(2-methoxyethyl)aminosulfur trifluoride (39 g, 134.4 mmol) slowly. Heat the resulting solution to 45° C. and stir for 16 hours. Pour the reaction slowly into ice water (50 mL). Adjust the pH of the solution to 7 with a saturated NaHCO$_3$ aqueous solution. Extract the aqueous solution with DCM (3×20 mL). Dry the combined organic extracts over sodium sulfate; filter; collect the filtrate; and concentrate the filtrate under reduced pressure. Purify the residue by flash chromatography eluting with a 4:1 ratio of petroleum ether to EtOAc to give the title compound (8.5 g, 74% yield) as a yellow liquid. $^1$H NMR (300 MHz, CDCl$_3$) δ 8.73 (d, J=2.4 Hz, 1H), 8.00 (dd, J=2.4, 8.1 Hz, 1H), 7.56 (d, J=8.1 Hz, 1H), 6.44-6.80 (t, J=54.9 Hz, 1 Hz).

PREPARATION 46

6-(Difluoromethyl)-N-methoxy-N-methyl-pyridine-3-carboxamide

Combine 5-bromo-2-(difluoromethyl)pyridine (5.00 g, 24.03 mmol), N,O-dimethylhydroxylamine hydrochloride (3.52 g, 36.09 mmol), palladium(II) acetate (0.162 g, 0.722 mmol), 4,5-bis(diphenylphosphino)-9,9-dimethylxanthene (0.695 g, 1.201 mmol), and potassium phosphate (tribasic) (15.3 g, 72.07 mmol) in m-xylene (50 mL). Purge the reaction vessel with carbon monoxide gas. Heat the solution to 100° C., and stir under an atmosphere of carbon monoxide for 16 hours. Safely purge the vessel in a well-ventilated area with nitrogen until it is free of carbon monoxide. Add water (200 mL) to quench the reaction. Adjust the pH of the mixture to 7 with a saturated sodium bicarbonate aqueous solution. Extract the mixture with EtOAc. Dry the combined organic extracts over sodium sulfate; filter; collect the filtrate; and concentrate the filtrate under reduced pressure. Purify the resulting residue by silica gel chromatography eluting with a 2:1 ratio of petroleum ether to EtOAc to give the title compound (2.5 g, 48% yield) as a clear oil. LCMS (m/z) 216 (M+1).

PREPARATION 47

Methyl 4-(difluoromethyl)benzoate

Dissolve p-carbomethoxybenzaldehyde (3.103 g, 18.713 mmol) in DCM (50 mL). Add bis(2-methoxyethyl)aminosulfur trifluoride (9.079 mL, 46.783 mmol), and stir 16 hours. Slowly pour the reaction mixture into a saturated aqueous NaHCO$_3$ aqueous solution (300 mL). Stir until gas evolution is complete (about 2 hours). Extract with DCM (2×100 mL). Dry the organic extracts over Na$_2$SO$_4$; filter; collect the filtrate; and concentrate the filtrate under reduced pressure. Purify by silica gel chromatography (Analogix® 80 g @ 55 mL/min) eluting with a gradient of hexanes to 20% ethyl acetate/hexanes over 30 minutes to give the title compound as a white solid (2.863 g, 82% yield). $^1$H NMR (400.15 MHz, d$_6$-DMSO) δ 8.08-8.06 (m, 2H), 7.70 (ddd, J=8.7, 1.1, 0.6 Hz, 2H), 7.26-6.98 (t, J=55.2 Hz, 1H), 3.86 (s, 3H).

PREPARATION 48

4-(Difluoromethyl)benzoic acid

Dissolve methyl 4-(difluoromethyl)benzoate (2.855 g, 15.336 mmol) in MeOH (30 mL). Add potassium hydroxide (8.41 mL 2 equivalents, 30.7 mmol), and stir the mixture for 16 hours. Concentrate the reaction mixture under reduced pressure, and add EtOAc (100 mL) and 1 N HCl (50 mL). Stir for 30 minutes. Separate the layers. Dry the organics over Na$_2$SO$_4$; filter; collect the filtrate; and concentrate the filtrate under reduced pressure to give the titled compound as a white solid (2.541 g, 96% yield). $^1$H NMR (399.83 MHz, d$_6$-DMSO) δ 13.29-13.28 (m, 1H), 8.04 (d, J=7.8 Hz, 2H), 7.67 (d, J=8.0 Hz, 2H), 7.24-6.97 (t, J=55.6, 1H).

PREPARATION 49

N-Methoxy-N-methyl-6-(trifluoromethyl)pyridine-3-carboxamide

Dissolve 6-(trifluoromethyl)pyridine-3-carboxylic acid (0.949 g, 4.767 mmol) in DMF (10 mL) and add N,O-dimethylhydroxylamine hydrochloride (0.590 g, 5.959 mmol), and DIPEA (1.67 mL, 9.534 mmol), followed by BOP (2.259 g, 5.005 mmol). Stir the resulting mixture for about 60 hours. Pour reaction mixture into water (200 mL). Extract with EtOAc (4×75 mL). Wash the combined organic extracts with a saturated sodium chloride aqueous solution (5×75 mL). Dry the organic extracts over sodium sulfate; filter; collect the filtrate; and concentrate the filtrate under reduced pressure. Dissolve the residue in EtOAc (100 mL). Sequentially wash the residue in EtOAc with a saturated NaHCO$_3$ aqueous solution (50 mL) to remove any residual acid starting material, followed by water (2×50 mL), and then a saturated sodium chloride aqueous solution (2×50 mL). Dry the organic layer over sodium sulfate; filter; collect the filtrate; and concentrate the filtrate under reduced pressure to give the title compound as a clear liquid (1.04 g, 93% yield). $^1$H NMR (400.43 MHz, d$_6$-DMSO) δ 8.90 (d, J=2.0 Hz, 1H), 8.25-8.23 (m, 1H), 7.96 (dd, J=0.7, 8.1 Hz, 1H), 3.52 (s, 3H), 3.27 (s, 3H).

Prepare the following compounds in Table 4 essentially by the method of Preparation 49 with the appropriate acid.

TABLE 4

| Prep. | Coupling Agent | Name | ES/MS (m/z) or $^1$H NMR |
|---|---|---|---|
| 50 | EDCI/HOBT | 2,3-Dichloro-N-methoxy-N-methyl-benzamide | $^1$H NMR (399.80 MHz, d$_6$-DMSO) δ 7.72-7.66 (m, 1H), 7.44-7.39 (m, 2H), 3.41 (s, 3H), 3.26 (s, 3H). |
| 51 | EDCI/HOBT | 2-Chloro-N-methoxy-N,3-dimethyl-benzamide | $^1$H NMR (399.80 MHz, d$_6$-DMSO) δ 7.41-7.36 (m, 1H), 7.27 (td, J = 7.4, 2.8 Hz, 1H), 7.22 (ddd, J = 7.6, 1.8, 0.5 Hz, 1H), 3.40 (s, 3H), 3.25-3.22 (m, 3H), 2.33 (s, 3H). |
| 52 | BOP | 4-(Difluoromethyl)-N-methoxy-N-methyl-benzamide | $^1$H NMR (400.15 MHz, d$_6$-DMSO) δ 7.69 (d, J = 8.5 Hz, 2H), 7.63 (d, J = 8.5 Hz, 2H), 7.22-6.94 (t, J = 55.6 Hz, 1H), 3.51 (s, 3H), 3.25 (s, 3H). |

PREPARATION 53

1-[6-(Trifluoromethyl)-3-pyridyl]ethanone

Dissolve N-methoxy-N-methyl-6-(trifluoromethyl)pyridine-3-carboxamide (0.685 g, 2.92 mmol) in THF (20 mL). Add methylmagnesium bromide (3.0 M in EtO$_2$, 1.950 mL, 5.850 mmol). Stir the mixture for 16 hours. Pour the reaction mixture into a saturated NaHCO$_3$ aqueous solution (20 mL). Extract with EtOAc (3×20 mL). Wash the combined organic extracts with water (30 mL) and saturated sodium chloride (2×30 mL). Dry the organic extracts over sodium sulfate; filter; collect the filtrate; and concentrate the filtrate under reduced pressure to give the title compound (0.545 g, 98%) as a light yellow solid. $^1$H NMR (400.43 MHz, d$_6$-DMSO) δ 9.21-9.21 (m, 1H), 8.51-8.49 (m, 1H), 8.03 (d, J=8.2 Hz, 1H), 2.64 (s, 3H).

Prepare the following compounds in Table 5 essentially by the method of Preparation 53 with the appropriate Weinreb Amide using ethyl magnesium bromide instead of methylmagnesium bromide.

TABLE 5

| Prep. | Name | ES/MS (m/z) or $^1$H NMR |
|---|---|---|
| 54 | 1-(2,3-Dichlorophenyl)propan-1-one | $^1$H NMR (399.80 MHz, d$_6$-DMSO) δ 7.72 (dd, J = 1.6, 8.0 Hz, 1H), 7.53 (dd, J = 1.6, 7.7 Hz, 1H), 7.43 (t, J = 7.8 Hz, 1H), 2.88 (q, J = 7.2 Hz, 2H), 1.04 (t, J = 7.2 Hz, 3H). |
| 55 | 1-(2-Chloro-3-methyl-phenyl)propan-1-one | $^1$H NMR (399.80 MHz, d$_6$-DMSO) δ 7.44-7.42 (m, 1H), 7.35-7.28 (m, 2H), 2.85 (q, J = 7.2 Hz, 2H), 2.34 (s, 3H), 1.04 (t, J = 7.2 Hz, 3H). |
| 56 | 1-[6-(Difluoromethyl)-3-pyridyl]propan-1-one | 186 (M + 1) |

PREPARATION 57

1-[6-(Trifluoromethyl)-3-pyridyl]propan-1-ol

Dissolve 6-trifluoromethyl-pyridine-3-carboxaldehyde (3.526 g, 20.136 mmol) in THF (50 mL). Add ethylmagnesium bromide (3.0 M in Et$_2$O, 7.38 mL, 22.1 mmol) quickly. Stir 30 minutes. Pour the reaction mixture into a saturated NaHCO$_3$ aqueous solution (100 mL). Extract with EtOAc (3×50 mL). Wash the combined organic extracts with a saturated NaCl aqueous solution (75 mL). Dry the organic extracts over Na$_2$SO$_4$; filter; collect the filtrate; and concentrate the filtrate under reduced pressure. Purify the residue by flash chromatography (Analogix® 40 g @ 40 mL/min) eluting with a gradient of EtOAc/hexanes (5% to 50%) over 30 minutes to give the title compound (2.01 g, 49% yield) as a yellow oil. $^1$H NMR (400.43 MHz, d$_6$-DMSO) δ 8.66 (d, J=1.6 Hz, 1H), 7.95 (dd, J=1.9, 8.1 Hz, 1H), 7.81 (d, J=8.0 Hz, 1H), 5.47 (d, J=4.5 Hz, 1H), 4.60 (q, J=5.8 Hz, 1H), 1.65-1.59 (m, 2H), 0.79 (t, J=7.4 Hz, 3H).

PREPARATION 58

1-[6-(Trifluoromethyl)-3-pyridyl]propan-1-one

Dissolve 1-[6-(trifluoromethyl)-3-pyridyl]propan-1-ol (2.010 g, 9.796 mmol) in DCM (40 mL). Add 3,3,3-Triacetoxy-3-iodophthalide (4.712 g, 10.776 mmol), and stir for 16 hours. Dilute with DCM (100 mL). Wash with 0.5 N NaOH (100 mL). Dry the organic extracts over Na$_2$SO$_4$; filter; collect the filtrate; and concentrate the filtrate under reduced pressure to give the title compound (1.910 g, 96% yield) as a white solid. $^1$H NMR (400.43 MHz, d$_6$-DMSO) δ 9.21 (dd, J=0.5, 1.4 Hz, 1H), 8.51-8.49 (m, 1H), 8.03 (dd, J=0.7, 8.1 Hz, 1H), 3.12 (q, J=7.1 Hz, 2H), 1.05 (t, J=7.1 Hz, 3H).

PREPARATION 59

1-[4-(Difluoromethyl)phenyl]ethanone

Dissolve 4-acetylbenzaldehyde (1.270 mL, 8.956 mmol) in DCM (20 mL). Add (3.963 g, 17.913 mmol), and stir for 5 days. Pour the reaction mixture slowly into a saturated sodium bicarbonate aqueous solution (250 mL). Stir the mixture until the gas evolution is complete (~2 hours). Extract with DCM (2×100 mL). Dry the organic extracts over Na$_2$SO$_4$; filter; collect the filtrate; and concentrate the filtrate under reduced pressure. Purify the residue by flash chromatography (Analogix® 40 g @ 40 mL/min) eluting with a gradient of hexanes to 20% EtOAc/hexanes over 30 minutes to give the title compound as a clear oil (0.714 g, 47% yield). $^1$H NMR (399.83 MHz, d$_6$-DMSO) δ 8.06 (d, J=8.1 Hz, 2H), 7.70 (d, J=8.1 Hz, 2H), 7.25-6.97 (t, J=55.6 Hz, 1H), 2.60 (s, 3H).

PREPARATION 60

1-[2-Methyl-4-(trifluoromethyl)phenyl]propan-1-one

Cool a solution of 1-bromo-2-methyl-4-(trifluoromethyl) benzene (2.00 g, 8.367 mmol) and THF (17 mL) to −71° C., and then add n-butyl lithium (2.5 M in hexanes, 9.204 mmol, 3.681 mL) over 5 minutes. Stir the mixture for 15 minutes at −71° C. Add N-methoxy-N-methylpropanamide (0.980 g, 8.367 mmol) to the mixture drop-wise over 3-4 minutes keeping temperature below −65° C. Continue to stir the solution at −71° C. for 15-20 minutes; then warm the solution to room temperature. Stir at room temperature for 40 minutes. Quench the reaction with a saturated ammonium chloride aqueous solution. Extract the aqueous layer with Et$_2$O. Wash the combined organic extracts with water and brine. Dry the mixture over sodium sulfate; filter; collect the filtrate; and concentrate the filtrate under reduced pressure. Purify the residue by flash chromatography (40 g RediSep® column) eluting with a gradient of 0-40% DCM/pentane to give the title compound as a colorless oil (1.490 g, 82% yield). $^1$H NMR (399.80 MHz, d$_6$-DMSO) δ 7.84 (d, J=7.8 Hz, 1H), 7.64-7.61 (m, 2H), 2.93 (q, J=7.1 Hz, 2H), 2.39 (s, 3H), 1.03 (t, J=7.2 Hz, 3H).

Prepare the following compounds in Table 6 essentially by the method of Preparation 60 with the appropriate aryl bromide.

TABLE 6

| Prep. | Name | ES/MS (m/z) or $^1$H NMR |
|---|---|---|
| 61 | 1-(3-Fluoro-4-methylphenyl)propan-1-one | $^1$H NMR (399.80 MHz, d$_6$-DMSO) δ 7.68 (dd, J = 1.7, 7.8 Hz, 1H), 7.63 (dd, J = 1.5, 10.6 Hz, 1H), 7.41 (t, J = 7.8 Hz, 1H), 2.99 (q, J = 7.2 Hz, 2H), 2.27 (d, J = 1.8 Hz, 3H), 1.04 (t, J = 7.2 Hz, 3H). |
| 62 | 1-(4-Fluoro-3-methylphenyl)propan-1-one | $^1$H NMR (399.80 MHz, d$_6$-DMSO) δ 7.89 (ddd, J = 7.6, 2.3, 0.6 Hz, 1H), 7.84-7.81 (m, 1H), 7.26-7.21 (m, 1H), 2.99 (q, J = 7.2 Hz, 2H), 2.26 (d, J = 1.9 Hz, 3H), 1.04 (t, J = 7.2 Hz, 3H). |
| 63 | 1-(2-Fluoro-3-methylphenyl)propan-1-one | $^1$H NMR (399.80 MHz, d$_6$-DMSO) δ 7.60-7.57 (m, 1H), 7.51-7.47 (m, 1H), 7.17 (t, J = 7.6 Hz, 1H), 2.94 (qd, J = 7.2, 2.8 Hz, 2H), 2.25 (d, J = 2.4 Hz, 3H), 1.04 (td, J = 7.1, 0.6 Hz, 3H). |

PREPARATION 64

2-Bromo-1-[4-(trifluoromethyl)phenyl]propan-1-one

Dissolve p-trifluoromethylpropiophenone (5.130 g, 25.120 mmol) in hydrogen bromide (30.00 mL) and acetic acid (20 mL). Add bromine (1.23 mL, 23.864 mmol) in acetic acid (25 mL) drop-wise over 30 minutes. Stir the reaction mixture for 48 hours, and dilute the reaction mixture with water (1 L) and EtOAc (250 mL). Add solid sodium carbonate portion-wise to adjust the pH to ~7 allowing the gas evolution to cease between additions. Extract the resulting mixture with EtOAc (2×250 mL). Dry the organic extracts over Na$_2$SO$_4$. Filter; collect the filtrate; and concentrate the filtrate under reduced pressure to give the title compound as a clear oil (7.140 g, 100% crude yield). $^1$H NMR (399.83 MHz, d$_6$-DMSO) δ 8.20 (dd, J=0.7, 8.8 Hz, 2H), 7.92-7.90 (m, 2H), 5.85 (q, J=6.5 Hz, 1H), 1.78 (d, J=6.5 Hz, 3H).

Prepare the following compounds in Table 7 essentially by the method of Preparation 64 with the appropriate ketone.

TABLE 7

| Prep. | Name | ES/MS (m/z) or $^1$H NMR |
|---|---|---|
| 65 | 2-Bromo-1-[6-(trifluoromethyl)-3-pyridyl]ethanone | $^1$H NMR (400.43 MHz, d$_6$-DMSO) 9.25 (d, J = 1.9 Hz, 1H), 8.56 (dd, J = 2.1, 8.1 Hz, 1H), 8.10-8.07 (m, 1H), 5.03 (s, 2H). |

TABLE 7-continued

| Prep. | Name | ES/MS (m/z) or $^1$H NMR |
|---|---|---|
| 66 | 2-Bromo-1-[6-(trifluoromethyl)-3-pyridyl]propan-1-one | $^1$H NMR (399.83 MHz, d$_6$-DMSO) δ 9.31 (dd, J = 0.8, 1.4 Hz, 1H), 8.64-8.62 (m, 1H), 8.10 (dd, J = 0.7, 8.2 Hz, 1H), 5.88 (q, J = 6.5 Hz, 1H), 1.80 (d, J = 6.5 Hz, 3H). |
| 67 | 2-Bromo-1-[4-(difluoromethyl)phenyl]ethanone | $^1$H NMR (399.83 MHz, d$_6$-DMSO) δ 8.12 (d, J = 8.7 Hz, 2H), 7.75-7.73 (m, 2H), 7.27-6.99 (m, 1H), 4.98 (s, 2H). |
| 68 | 2-Bromo-1-[4-(difluoromethyl)phenyl]propan-1-one | $^1$H NMR (399.80 MHz, d$_6$-DMSO) δ 8.14 (d, J = 8.5 Hz, 2H), 7.73 (d, J = 8.3 Hz, 2H), 7.25-6.97 (m, 1H), 5.82 (q, J = 6.5 Hz, 1H), 1.77 (d, J = 6.5 Hz, 3H). |
| 69 | 2-Bromo-1-[6-(difluoromethyl)-3-pyridyl]propan-1-one | 264/266 (M + 1 Br$^{79}$/Br$^{81}$) |

Alternate Preparation 70

2-Bromo-1-[4-(trifluoromethyl)phenyl]propan-1-one

Add p-trifluoromethylpropiophenone (75 g, 360 mmol, 1.0 equiv) to acetic acid (375 mL). Add bromine (18.1 mL, 352 mmol, 0.98 equiv) in acetic acid (375 mL) in a drop-wise fashion over 45 minutes. After completion of the addition, warm the mixture to an internal temperature of 40° C., and stir for 90 minutes. Remove the volatile components under reduced pressure, and dissolve the residue in Et$_2$O (300 mL). Treat with a saturated sodium bicarbonate aqueous solution (4×200 mL) being cautious of vigorous gas evolution. Separate the organic phase, and dry over MgSO$_4$. Remove the solids by filtration; collect the filtrate; and concentrate the filtrate under reduced pressure to give the title compound as a colorless oil which solidifies on standing (93 g, 92.0% yield). $^1$H NMR (400 MHz, d$_6$-DMSO) δ 8.13 (d, J=8.3 Hz, 2H), 7.76 (d, J=8.3 Hz, 2H), 5.27 (q, J=6.5 Hz, 1H), 1.93 (d, J=6.5 Hz, 3H).

PREPARATION 71

2-Bromo-1-[2-methyl-4-(trifluoromethyl)phenyl]propan-1-one

Add 1-[2-methyl-4-(trifluoromethyl)phenyl]propan-1-one (0.805 g, 3.723 mmol), N-bromosuccinimide (0.662 g, 3.723 mmol), SCX-2® (1 mmol/g; 0.298 g, 0.298 mmol), and Et$_2$O (11 mL) to a screw cap vial equipped with a stir bar. Stir the reaction at room temperature for 2 hours. Add N-bromosuccinimide (0.663 g, 3.723 mmol) and continue stirring at room temperature for 2 hours. Add more N-bromosuccinimide (0.663 g, 3.723 mmol), and continue stirring at room temperature for an additional 2 hours. Filter the reaction, and wash the solids with ample Et$_2$O. Collect the filtrate, and concentrate the filtrate under reduced pressure. Place the resulting mixture in a freezer overnight. Purify the resulting material by flash chromatography (120 RediSep® silica gel column) eluting with a gradient of 0-30% DCM/pentane to give the title compound as a colorless oil (0.820 g, 75% yield). $^1$H NMR (399.80 MHz, d$_6$-DMSO) δ 7.95 (d, J=8.0 Hz, 1H), 7.69-7.65 (m, 2H), 5.64 (q, J=6.5 Hz, 1H), 2.39 (s, 3H), 1.74 (d, J=6.5 Hz, 3H).

Prepare the following compounds in Table 8 essentially by the method of Preparation 71 with the appropriate ketone.

TABLE 8

| Prep. | Name | ES/MS (m/z) or $^1$H NMR |
|---|---|---|
| 72 | 2-Bromo-1-(4-fluoro-3-methyl-phenyl)propan-1-one | $^1$H NMR (399.80 MHz, d$_6$-DMSO) δ 7.99-7.97 (m, 1H), 7.93-7.89 (m, 1H), 7.31-7.26 (m, 1H), 5.78 (q, J = 6.5 Hz, 1H), 2.27 (d, J = 1.9 Hz, 3H), 1.73 (d, J = 6.5 Hz, 3H). |
| 73 | 2-Bromo-1-(2-fluoro-3-methyl-phenyl)propan-1-one | $^1$H NMR (399.80 MHz, d$_6$-DMSO) δ 7.71-7.66 (m, 1H), 7.55-7.51 (m, 1H), 7.21 (t, J = 7.7 Hz, 1H), 5.50 (q, J = 6.5 Hz, 1H), 2.26 (d, J = 2.3 Hz, 3H), 1.74 (d, J = 6.5 Hz, 3H). |
| 74 | 2-Bromo-1-(3-fluoro-4-methyl-phenyl)propan-1-one | $^1$H NMR (399.80 MHz, d$_6$-DMSO) δ 7.78-7.72 (m, 2H), 7.47-7.43 (m, 1H), 5.79 (q, J = 6.5 Hz, 1H), 2.29 (d, J = 1.8 Hz, 3H), 1.73 (d, J = 6.5 Hz, 3H). |
| 75 | 2-Bromo-1-(2-fluorophenyl)propan-1-one | $^1$H NMR (399.80 MHz, d$_6$-DMSO) δ 7.90-7.86 (m, 1H), 7.68-7.64 (m, 1H), 7.36-7.33 (m, 2H), 5.51-5.46 (m, 1H), 1.74 (d, J = 6.5 Hz, 3H). |
| 76 | 2-Bromo-1-(3-fluorophenyl)propan-1-one | $^1$H NMR (399.80 MHz, d$_6$-DMSO) δ 7.85 (dt, J = 7.6, 1.3 Hz, 1H), 7.78 (ddd, J = 9.9, 2.6, 1.7 Hz, 1H), 7.58 (td, J = 8.0, 5.8 Hz, 1H), 7.52-7.48 (m, 1H), 5.80 (q, J = 6.5 Hz, 1H), 1.74 (d, J = 6.4 Hz, 3H). |

TABLE 8-continued

| Prep. | Name | ES/MS (m/z) or $^1$H NMR |
|---|---|---|
| 77 | 2-Bromo-1-(2,3-difluorophenyl)propan-1-one | $^1$H NMR (399.80 MHz, d$_6$-DMSO) δ 7.73-7.70 (m, 2H), 7.34 (td, J = 8.1, 3.2 Hz, 1H), 5.49 (q, J = 6.5 Hz, 1H), 1.74 (d, J = 6.5 Hz, 3H). |
| 78 | 2-Bromo-1-(3,4-difluorophenyl)propan-1-one | $^1$H NMR (399.80 MHz, d$_6$-DMSO) δ 8.07 (ddd, J = 11.4, 7.8, 2.2 Hz, 1H), 7.94-7.92 (m, 1H), 7.65-7.59 (m, 1H), 5.81 (q, J = 6.5 Hz, 1H), 1.75 (d, J = 6.4 Hz, 3H). |
| 79 | 2-Bromo-1-(2,3-dichlorophenyl)propan-1-one | $^1$H NMR (399.80 MHz, d$_6$-DMSO) δ 7.76 (dd, J = 1.3, 8.0 Hz, 1H), 7.69 (dd, J = 1.3, 7.7 Hz, 1H), 7.44 (t, J = 7.9 Hz, 1H), 5.51 (q, J = 6.5 Hz, 1H), 1.72 (d, J = 6.6 Hz, 3H). |
| 80 | 2-Bromo-1-(3,4-dichlorophenyl)propan-1-one | $^1$H NMR (399.80 MHz, d$_6$-DMSO) δ 8.21 (d, J = 2.1 Hz, 1H), 7.95 (dd, J = 2.0, 8.4 Hz, 1H), 7.81 (d, J = 8.5 Hz, 1H), 5.82 (q, J = 6.5 Hz, 1H), 1.73 (d, J = 6.5 Hz, 3H). |
| 81 | 2-Bromo-1-(2-chloro-3-methyl-phenyl)propan-1-one | $^1$H NMR (399.80 MHz, d$_6$-DMSO) δ 7.54-7.50 (m, 2H), 7.33 (t, J = 7.6 Hz, 1H), 5.50 (q, J = 6.6 Hz, 1H), 2.35 (s, 3H), 1.75 (d, J = 6.6 Hz, 3H). |

PREPARATION 82

N-[5-[6-(Difluoromethyl)-3-pyridyl]-4-methyl-1H-imidazol-2-yl]acetamide

Dissolve 2-bromo-1-[6-(difluoromethyl)-3-pyridyl]propan-1-one (0.500 g, 1.89 mmol) and acetyl guanidine (0.514 g, 5.68 mmol) in DMF (12 mL). Heat the mixture to 50° C., and stir for 16 hours. Pour the mixture into water, and extract with EtOAc (3×20 mL). Dry the combined organic extracts over sodium sulfate; filter; collect the filtrate; and concentrate the filtrate under reduced pressure. Purify the resulting residue by flash chromatography (silca gel) eluting with a 40:1 ratio of DCM/MeOH to give the title compound as a white solid (0.229 g, 46% yield). LCMS (m/z) 267 (M+1).

PREPARATION 83

2-Methyl-3-[4-(trifluoromethyl)phenyl]imidazo[1,2-a]pyrimidine

Stir a mixture of 2-bromo-1-[4-(trifluoromethyl)phenyl]propan-1-one (500 g, 1.78 mol, 1 equiv), IPA (5 L), 2-aminopyrimidine (205 g, 2.13 mol, 1.2 equiv), and sodium bicarbonate (298.8 g, 3.55 mol, 2 equiv) in a thermally controlled reactor at 80° C. for 18 hours. Cool the suspension, and concentrate in vacuo. Dilute the resulting mixture with DCM (5 L), and the wash with brine (2 L). Re-extract the brine wash with DCM (2.5 L); combine all the organic extracts; dry over MgSO$_4$; filter; collect the filtrate; and concentrate the filtrate under reduced pressure to a red gum. Slurry the resulting red gum in Et$_2$O (1.5 L); filter; and collect the solid. Air dry the solid for 45 min to give the product as a fine off-white solid (108 g, 22% yield). ES/MS (m/z) 278 (M+1).

Alternate Preparation 83

2-Methyl-3-[4-(trifluoromethyl)phenyl]imidazo[1,2-a]pyrimidine

Dissolve 2-bromo-1-[4-(trifluoromethyl)phenyl]propan-1-one (7.120 g, 25.332 mmol), and 2-aminopyrimidine (5.464 g, 55.729 mmol) in EtOH (40 mL). Heat the mixture to reflux, and stir for 24 hours. Cool to room temperature, and concentrate under reduced pressure. Dissolve the residue in EtOAc (750 mL). Sequentially wash the organic extracts with a saturated NaS$_2$O$_3$ aqueous solution (250 mL), a saturated NaHCO$_3$ aqueous solution (250 mL), and a saturated NaCl aqueous solution (350 mL). Crystallize the orange residue from heptanes/EtOAc. Collect the title compound as a white solid (3.290 g, 46.85% yield). $^1$H NMR (399.83 MHz, d$_6$-DMSO) δ 8.84 (dd, J=1.9, 7.0 Hz, 1H), 8.54 (dd, J=2.0, 4.2 Hz, 1H), 8.06-8.04 (m, 2H), 7.83-7.81 (m, 2H), 7.10 (dd, J=4.1, 6.9 Hz, 1H), 2.68 (s, 3H). ES/MS (m/z) 277.99.

Prepare the following compounds in Table 9 essentially by the method of Preparation 83 with the appropriate α-bromo ketone or α-chloro ketone.

TABLE 9

| Prep. | Name | ES/MS (m/z) or $^1$H NMR |
|---|---|---|
| 84 | 3-[6-(Trifluoromethyl)-3-pyridyl]imidazo[1,2-a]pyrimidine | $^1$H NMR (400.43 MHz, DMSO-d6): δ 9.34-9.34 (m, 1H), 9.01-8.98 (m, 1H), 8.61-8.56 (m, 3H), 7.98-7.95 (m, 1H), 7.10-7.07 (m, 1H). |
| 85 | 2-Methyl-3-[6-(trifluoromethyl)-3-pyridyl]imidazo[1,2-a]pyrimidine | 279 (M + 1) |

TABLE 9-continued

| Prep. | Name | ES/MS (m/z) or $^1$H NMR |
|---|---|---|
| 86 | 3-[4-(Difluoromethyl)phenyl]imidazo[1,2-a]pyrimidine | $^1$H NMR (399.83 MHz, d$_6$-DMSO) δ 8.98 (dd, J = 2.0, 6.8 Hz, 1H), 8.55 (dd, J = 2.0, 4.1 Hz, 1H), 8.46 (s, 1H), 8.15-8.13 (m, 2H), 7.66 (d, J = 8.2 Hz, 2H), 7.21-6.93 (m, 2H). |
| 87 | 3-[4-(Difluoromethyl)phenyl]-2-methyl-imidazo[1,2-a]pyrimidine | 260 (M + 1) |
| 88* | 3-(4-Fluorophenyl)-2-methyl-imidazo[1,2-a]pyrimidine | $^1$H NMR (399.83 MHz, d$_6$-DMSO) δ 8.80 (dd, J = 2.0, 6.9 Hz, 1H), 8.50 (dd, J = 2.0, 4.1 Hz, 1H), 7.87-7.83 (m, 2H), 7.33-7.28 (m, 2H), 7.07 (dd, J = 4.1, 6.8 Hz, 1H), 2.62 (s, 3H). |
| 89* | 3-(4-Bromophenyl)-2-methyl-imidazo[1,2-a]pyrimidine | $^1$H NMR (399.83 MHz, d$_6$-DMSO) δ 8.82 (dd, J = 2.0, 6.9 Hz, 1H), 8.53 (dd, J = 1.9, 4.1 Hz, 1H), 7.81-7.78 (m, 2H), 7.70-7.67 (m, 2H), 7.09 (dd, J = 4.1, 6.9 Hz, 1H), 2.65 (s, 3H). |

*α-chloro ketone used.

PREPARATION 90

2-Methyl-3-(p-tolyl)imidazo[1,2-a]pyrimidine

Add 3-(4-bromophenyl)-2-methyl-imidazo[1,2-a]pyrimidine (1.00 g, 3.470 mmol) and DMF (17 mL) to a 50 mL screw-cap vial (fitted with stir bar). Degas the solution with nitrogen for 3 min. Add tetramethylstannane (1.91 mL, 13.88 mmol) and bis(triphenylphosphine)palladium(II) chloride (0.36 g, 520.57 μmol) to the vial, and close the vial. Heat the mixture in an oil bath to 130° C. for 2 hours. Cool the reaction to room temperature, and quench with an excess of water. Extract the mixture with EtOAc. Wash the combined organic extracts with brine. Dry the organic extracts over potassium carbonate; filter; collect the filtrate; and concentrate the filtrate under reduced pressure. Purify the crude mixture by silica gel chromatography with a gradient of 50-100% hexane/EtOAc to give the title compound as a white solid (0.50 g, 64% yield). LCMS (m/z) 224.2 (M+1). $^1$H NMR (399.83 MHz, d6-DMSO) δ 8.81-8.79 (m, 1H), 8.51-8.49 (m, 1H), 7.73 (d, J=7.9 Hz, 2H), 7.31 (d, J=7.9 Hz, 2H), 7.09-7.06 (m, 1H), 2.64 (s, 3H), 2.36 (s, 3H).

PREPARATION 91

5-[6-(Difluoromethyl)-3-pyridyl]-4-methyl-1H-imidazol-2-amine

Dissolve N-[5-[6-(difluoromethyl)-3-pyridyl]-4-methyl-1H-imidazol-2-yl]acetamide (0.172 g, 0.65 mmol) in MeOH (5 mL) and water (5 mL). Heat the mixture to 60° C. Add hydrochloric acid (12 N, 5 mL, 60 mmol). Stir mixture for 2 hours at 60° C. Concentrate the mixture to a volume of about 10 mL. Adjust the pH of the aqueous solution to 8. Extract the resulting solution with EtOAc (2×20 mL). Dry the combined organic extracts over sodium sulfate; filter; collect the filtrate; and concentrate the filtrate under reduced pressure to give the title compound as a yellow oil (0.153 g, 100% crude yield). LCMS (m/z) 225 (M+1).

PREPARATION 92

[4-Methyl-5-[4-(trifluoromethyl)phenyl]-1H-imidazol-2-yl]ammonium formate

Suspend 2-methyl-3-[4-(trifluoromethyl)phenyl]imidazo[1,2-a]pyrimidine (2.176 g, 7.849 mmol) in EtOH (15.00 mL, 257.646 mmol). Add hydrazine hydrate (4.00 mL, 81.821 mmol). Heat to 125° C. with microwave irradiation. Stir for 30 minutes, and concentrate under reduced pressure. Dissolve the residue in EtOAc (75 mL); wash the organic extracts with water (3×50 mL); and then wash with a saturated NaCl aqueous solution (50 mL). Dry the organic extracts over Na$_2$SO$_4$; filter; collect the filtrate; and concentrate the filtrate in vacuo. Purify by reverse phase flash chromatography (Analogix® 150 g @ 40 mL/min) eluting with a gradient of 5-30% ACN/water over 35 minutes. Material precipitates upon loading samplet. Collect the resulting white material from the samplet and reflux it MeOH for 15 minutes. Filter the MeOH mixture through diatomaceous earth collect the filtrate, and wash the diatomaceous earth with MeOH. Concentrate the combined filtrates under reduced pressure to give the title compound (1.643 g, 72.9% yield) as a white crystalline solid. $^1$H NMR (400.43 MHz, d$_6$-DMSO) δ 13.14-13.11 (m, 2H), 7.77 (d, J=8.4 Hz, 2H), 7.66 (d, J=8.2 Hz, 2H), 7.47 (s, 2H), 2.26 (s, 3H). ES/MS (m/z) 241.99 (parent+1, formate not detected).

PREPARATION 93

4-Methyl-5-[4-(trifluoromethyl)phenyl]-1H-imidazol-2-amine; oxalic acid

Add 2-Methyl-3-[4-(trifluoromethyl)phenyl]imadazo[1,2-A]pyrimidine (50 g, 0.180 mol), ACN (500 mL), and hydrazine monohydrate (20.1 g 0.628 mol) together at 25 to 30° C. Heat the reaction mixture to 78 to 82° C., and stir for 40 to 48 hours. Monitor the reaction progress by HPLC. When the reaction is complete, cool the mixture to 40 to 45° C.; concentrate to 100 mL of residual volume; and remove residual moisture by azeotrope distillation with toluene (3×250 mL). Cool the reaction mixture to 25 to 30° C.; add DCM (250 mL); then stir the mixture for 15 minutes. Add water (500 mL) to the mixture, and stir for 30 minutes. Separate the layers, and wash the organic layer with water (4×500 mL). Concentrate the organic layer under reduced pressure at 30 to 40° C. to 50 mL of residual volume to give the crude base. Cool this mixture to 25 to 30° C., and add MeOH (100 mL). Add a solution of oxalic acid dihydrate (45.5 g, 0.500 mol) in MeOH (300 mL) over 60 minutes, and stir the mixture for 2 hours at 25 to 30° C. Cool the slurry to 0 to 5° C., and stir for one hour. Filter the mixture; wash the solid with MeOH (100 mL); collect solid; and dry the solid under vacuum at 45 to 50° C.

for 12 hours to give the title compound (41.0 g, 78% yield). $^1$H NMR (300 MHz, d$_6$-DMSO) δ 7.82 (d, J=8.4 Hz, 2H), 7.69 (d, J=8.1 Hz, 2H), 2.32 (s, 3H).

PREPARATION 94

4-Methyl-5-[2-methyl-4-(trifluoromethyl)phenyl]-1H-imidazol-2-amine

Add 2-bromo-1-(2,3-dichlorophenyl)propan-1-one (0.214 g, 0.759 mmol), 2-aminopyrimidine (0.123 g, 1.290 mmol) and ACN (1.5 mL) to a microwave vessel (equipped with a stir bar). Heat the mixture to 140° C. with microwave irradiation, and stir for 45 minutes. Cool the mixture to room temperature, and add hydrazine (0.23 mL, 4.554 mmol). Heat the mixture to 100° C. with microwave irradiation while stirring for 30 minutes. Dilute the reaction with water, and extract the aqueous mixture with EtOAc. Wash the organic extracts with water; collect extracts; and dry the extracts over sodium sulfate; filter; collect the filtrate; and concentrate the filtrate under reduced pressure. Purify the material on an SCX-2® column (10 g) with DCM. Rinse the column with DCM, 40% MeOH in DCM, 80% MeOH in DCM then elute the product with 50% DCM/7 M ammonia in MeOH. Concentrate the ammonia fraction under reduced pressure. Purify the residue by radial chromatography on a 2 mm silica gel plate eluting with a gradient of 75%-100% EtOAc/hexane, then gradient of 1-4% 7 M NH$_3$ in MeOH in EtOAc to give the title compound as a light beige foam (0.042 g, 23% yield). $^1$H NMR (399.80 MHz, d$_6$-DMSO) δ 10.50-10.48 (m, 1H), 7.45-7.42 (m, 1H), 7.25-7.23 (m, 2H), 5.07 (s, 2H), 1.89 (s, 3H).

Prepare the following compounds in Table 10 essentially by the method of Preparation 94 using the appropriate α-bromo ketone.

TABLE 10

| Prep. | Name | ES/MS (m/z) or $^1$H NMR |
|---|---|---|
| 95 | 5-(4-Chlorophenyl)-4-methyl-1H-imidazol-2-amine | |
| 96 | 5-(3-Chlorophenyl)-4-methyl-1H-imidazol-2-amine | 208/210 (M + 1 Cl$^{35}$/Cl$^{37}$) |
| 97 | 5-(3-Fluoro-4-methyl-phenyl)-4-methyl-1H-imidazol-2-amine | 206 (M + 1) |
| 98 | 4-Methyl-5-[2-methyl-4-(trifluoromethyl)phenyl]-1H-imidazol-2-amine | 256 (M + 1) |
| 100 | 5-[2-Fluoro-4-(trifluoromethyl)phenyl]-4-methyl-1H-imidazol-2-amine | 260 (M + 1) |
| 101 | 5-(3-Fluorophenyl)-4-methyl-1H-imidazol-2-amine | 192 (M + 1) |
| 102 | 5-(3-Chloro-4-methyl-phenyl)-4-methyl-1H-imidazol-2-amine | 222/224 (M + 1 Cl$^{35}$/Cl$^{37}$) |
| 103 | 5-(2,3-Difluorophenyl)-4-methyl-1H-imidazol-2-amine | 210 (M + 1) |
| 104 | 5-(3,4-Difluorophenyl)-4-methyl-1H-imidazol-2-amine | 210 (M + 1) |
| 105 | 5-(3,4-Dichlorophenyl)-4-methyl-1H-imidazol-2-amine | 241/242/243/244 [(M + 1 (2Cl$^{35}$/Cl$^{37}$)] |

TABLE 10-continued

| Prep. | Name | ES/MS (m/z) or $^1$H NMR |
|---|---|---|
| 106 | 5-(2-Fluoro-3-methyl-phenyl)-4-methyl-1H-imidazol-2-amine | 205 (M + 1) |
| 107 | 5-(2-Chloro-3-methyl-phenyl)-4-methyl-1H-imidazol-2-amine | 222/224 (M + 1 Cl$^{35}$/Cl$^{37}$) |
| 108 | 5-(2-Fluorophenyl)-4-methyl-1H-imidazol-2-amine | 192 (M + 1) |

PREPARATION 109 tert-Butyl N-[[6-(difluoromethyl)-5-[[4-methyl-5-[4-(trifluoromethyl)phenyl]-1H-imidazol-2-yl]carbamoyl]-3-pyridyl]methyl]carbamate Dissolve [4-methyl-5-[4-(trifluoromethyl)phenyl]-1H-imidazol-2-yl]ammonium formate (0.205 g, 0.714 mmol) and 5-[(tert-butoxycarbonylamino)methyl]-2-(difluoromethyl)pyridine-3-carboxylic acid (0.283 g, 0.749 mmol) in DCM (5 mL). Add DIPEA (0.50 mL, 2.855 mmol) followed by BOP (0.350 g, 0.792 mmol). Heat the mixture to 60° C., and stir 16 hours. Add benzotriazol-1-yloxy-tris(dimethylamino)phosphonium hexafluorophosphate (0.150 g, 0.339 mmol). Stir the mixture for 2 hours. Pour the reaction mixture into water (15 mL). Extract with EtOAc (3×15 mL, and sequentially wash the combined organics with a saturated sodium chloride aqueous solution (4×15 mL) and a saturated sodium bicarbonate aqueous solution (15 mL). Dry the organic extracts over sodium sulfate; filter; collect the filtrate; and concentrate the filtrate under reduced pressure. Purify the residue by reverse phase flash chromatography (Analogix® 55 g @ 40 mL/min) eluting with a gradient of 5-75% ACN/water over 30 minutes. Concentrate the appropriate fractions under reduced pressure until only water remains and the product is a suspended solid. Add a saturated NaHCO$_3$ aqueous solution (50 mL), and extract with EtOAc (2×30 mL) to give the title compound (0.212 g, 56%) as a white solid. LCMS (m/z) 526 (M+1) 524 (M–1).

PREPARATION 110

5-(Aminomethyl)-2-(difluoromethyl)-N-[4-methyl-5-[4-(trifluoromethyl)phenyl]-1H-imidazol-2-yl]pyridine-3-carboxamide Add hydrochloric acid (10 mL, 40.0 mmol, 4 M in 1,4 dioxane) to tert-butyl N-[[6-(difluoromethyl)-5-[[4-methyl-5-[4-(trifluoromethyl)phenyl]-1H-imidazol-2-yl]carbamoyl]-3-pyridyl]methyl]carbamate (0.212 g, 0.403 mmol) and stir overnight. Dilute with water, and extract with Et$_2$O. Adjust the pH to ~8 with a saturated sodium bicarbonate aqueous solution. Extract with EtOAc (3×30 mL). Dry the organic extracts over sodium sulfate; filter; collect the filtrate; and concentrate the filtrate under reduced pressure. Purify by reverse phase flash chromatography (Analogix® 40 g @ 40 mL/min) eluting with a gradient of 2-55% ACN/water over 30 minutes. Concentrate the appropriate fractions under reduced pressure until all the ACN is removed and only water remains. Add a saturated sodium bicarbonate aqueous solution (30 mL), and extract with EtOAc (3×20 mL). Dry the organic extracts over sodium sulfate; filter; collect the filtrate; and concentrate the filtrate under reduced pressure to give the title compound as a light yellow solid (0.098 g, 57% yield). $^1$H NMR (400.43 MHz, d$_6$-DMSO) δ 8.71-8.69 (m, 1H), 8.16 (s, 1H), 7.79-7.77 (m, 2H), 7.69-7.67 (m, 2H), 7.42-7.28 (m, 1H), 3.81 (s, 2H), 2.43 (s, 3H).

EXAMPLE 1

2-(Difluoromethyl)-5-{[(2-methylpropanoyl)amino]methyl}-N-{4-methyl-5-[4-(trifluoromethyl)phenyl]-1H-imidazol-2-yl}pyridine-3-carboxamide

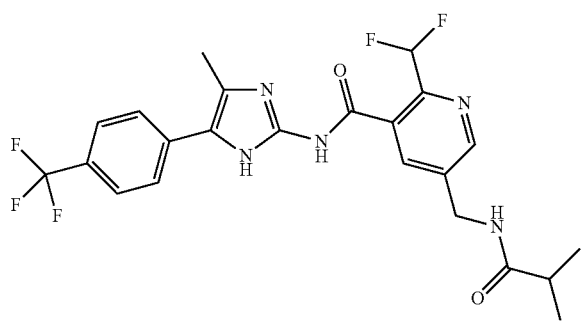

In a thermally controlled reactor stir a mixture of 4-methyl-5-[4-(trifluoromethyl)phenyl]-1H-imidazol-2-amine (395 g, 1.63 mol, 1 equiv), 2-(difluoromethyl)-5-{[(2-methylpropanoyl)amino]methyl}pyridine-3-carboxylic acid (445.8 g, 1.63 mol, 1 equiv), DMF (3.16 L), DIPEA (856 ml, 4.91 mol, 3 equiv) and TBTU (630 g, 1.965 mol, 1.2 equiv) at an internal temperature of 75° C. for 18 hours. Cool the mixture; dilute with EtOAc (2.5 L); and wash with water (3×5 L) and brine (2×2.5 L). Extract the combined aqueous phases with EtOAc (2.5 L). Combine the organic extracts, and dry over $MgSO_4$. Concentrate to dryness to give a yellow semi-solid. Slurry this solid with $Et_2O$ (2.5 L) for 3 hours; collect the solids by filtration; and air dry for 16 hours then in vacuo at 50° C. for a further 48 hours to give the title product as a fine free flowing white solid (568 g, 66% yield). $^1$H NMR (MeOD-$d_4$, 500 MHz): δ 8.63 (s, 1H), 8.13 (s, 1H), 7.74 (d, 2H, J=8.1 Hz), 7.67 (d, 2H, J=8.1 Hz), 7.36 (t, 1H, J=54.2 Hz), 4.47 (s, 2H), 2.52-2.45 (m, 4H), 1.13 (d, 6H, J=6.8 Hz); MS (m/z) 496 (M+1).

ALTERNATE PROCEDURE A, EXAMPLE 1

Add 2-(Difluoromethyl)-5-{[(2-methylpropanoyl)amino]methyl}pyridine-3-carboxylic acid (230 g, 0.845 mol, 1 eq), 4-methyl-5-[4-(trifluoromethyl)phenyl]-1H-imidazol-2-amine (280.6 g, 0.845 mol, 1 eq), and 4-methylmorpholine (427.8 g, 4.22 mol, 5 eq) to EtOAc, (2.5 L). Stir the reaction mixture at 15-25° C. for 1 h. Add propylphosphonic anhydride (T3P®) (50% w/w in EtOAc, 1.884 kg, 2.95 mol, 3.5 eq) over 17 min while maintaining the temperature≤40° C. Rinse the addition vessel with EtOAc (415 mL), and add the rinses to the reaction mixture. Stir the reaction mixture at 15-25° C. for 1 h, and then heat to 65-75° C. overnight. Cool the reaction mixture to 15-25° C., and dilute with EtOAc (3 L). Wash the reaction mixture with water, (2×2 L). Sequentially wash the organic phase with 1 N HCl (2×2 L), brine (2 L), 10% $Na_2CO_3$ aqueous solution (2×2 L), and deionized water (2×2 L). Concentrate the organic layer under vacuum at 65° C. until solids are observed (about 4 L, 62% volume removed). Add absolute EtOH (3 L), and re-concentrate the solution to about 3 L. Add absolute EtOH (1 L), and stir the slurry at 65-75° C. for 30 min then at 15-25° C. for approximately 63 hours. Cool the slurry to −15 to −5° C. while stirring for ≥2 h. Isolate the solid by filtration, and rinse the solid with cold absolute EtOH (−10° C., 420 mL). Dry the resulting solid under vacuum at 50° C. for 2 nights to give the title compound (268 g, 64% yield). $^1$H NMR (400 MHz, $d_6$-DMSO) δ 12.09 (s, broad, 2H), 8.66 (s, 1H), 8.44 (t, J=5.6 Hz, 1H), 8.07 (s, 1H), 7.78 (dd, J=38.6 and 8.2 Hz, 4H), 7.37 (t, J=54.3 Hz, 1H), 4.40 (d, J=5.6 Hz, 2H), 2.46 (s, 3H), 2.46 (m, J=6.8 Hz, 1H), 1.05 (d, J=6.8 Hz, 6H).

ALTERNATE PROCEDURE B, EXAMPLE 1

Dissolve [4-methyl-5-[4-(trifluoromethyl)phenyl]-1H-imidazol-2-yl]ammonium formate (1.011 g, 1.00 equiv, 3.520 mmol), and 2-(difluoromethyl)-5-[2-methylpropanoylamino)methyl]pyridine-3-carboxylic acid (1.497 g, 1.25 equiv, 4.400 mmol) in DMF (25.00 mL, 323.313 mmol). Add DIPEA (2.46 mL, 14.079 mmol), followed by BOP (2.065 g, 4.576 mmol). Heat to 60° C., and stir overnight. Pour the reaction mixture into water (200 mL). Extract the mixture with EtOAc (3×75 mL). Wash the combined organic extracts with a saturated NaCl aqueous solution (4×100 mL), then a saturated $NaHCO_3$ aqueous solution (100 mL). Dry the organics over $Na_2SO_4$; filter; collect the filtrate; and concentrate the filtrate in vacuo. Purify by flash chromatography (Analogix® 80 g @ 55 mL/min) eluting with a gradient of DCM to 8% 7 N $NH_3$ in MeOH/DCM over 40 minutes. Collect 1.592 g of material. Crystallize from EtOAc/MeOH/heptanes. Filter the solid product washing with hexanes and dry under vacuum overnight to give the title compound (1.298 g, 74.43% yield) as a white solid. $^1$H NMR (400.43 MHz, $d_6$-DMSO) δ 12.34-12.26 (m, 2H), 8.61 (d, J=1.8 Hz, 1H), 8.41-8.37 (m, 1H), 8.05-8.02 (m, 1H), 7.77 (d, J=8.2 Hz, 2H), 7.70-7.68 (m, 2H), 7.56-7.50 (m, 1H), 4.34 (d, J=5.7 Hz, 2H), 2.42-2.38 (m, 1H), 1.00 (d, J=6.9 Hz, 6H). ES/MS (m/z) 496.17.

Prepare the following compounds in Table 11 essentially by the alternate procedure B of Example 1 with the appropriate 2-aminoimidazole (or salt thereof) and acid.

TABLE 11

| Ex | Coupling Agent | Name | Structure | ES/MS (m/z) or $^1$H NMR |
|---|---|---|---|---|
| 2 | BOP | 2-Chloro-5-[(2-methylpropanoylamino)methyl]-N-[4-methyl-5-[6-(trifluoromethyl)-3-pyridyl]-1H-imidazol-2-yl]benzamide | 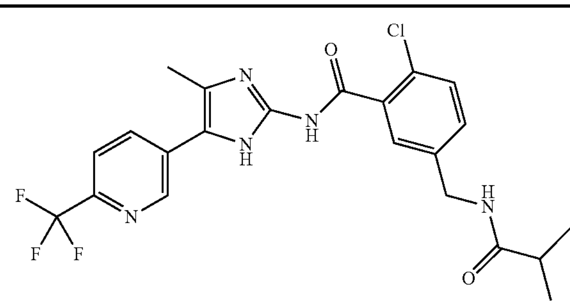 | 480/482 (M + 1 $Cl^{35}/Cl^{37}$) |

TABLE 11-continued

| Ex | Coupling Agent | Name | Structure | ES/MS (m/z) or $^1$H NMR |
|---|---|---|---|---|
| 3 | BOP | 2-Chloro-5-[(2,2-dimethylpropanoylamino)methyl]-N-[4-methyl-5-[6-(trifluoromethyl)-3-pyridyl]-1H-imidazol-2-yl]benzamide | 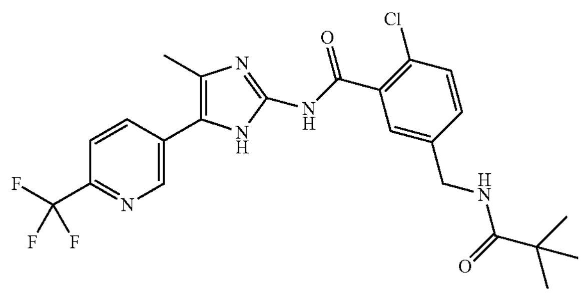 [SMILES: Cc1nc(NC(=O)c2cc(CNC(=O)C(C)(C)C)ccc2Cl)[nH]c1-c1ccc(C(F)(F)F)nc1] | 494/496 (M + 1 Cl$^{35}$/Cl$^{37}$) |
| 4 | BOP | 2-(Difluoromethyl)-N-[5-[6-(difluoromethyl)-3-pyridyl]-4-methyl-1H-imidazol-2-yl]-5-[(2-methylpropanoylamino)methyl]benzamide | 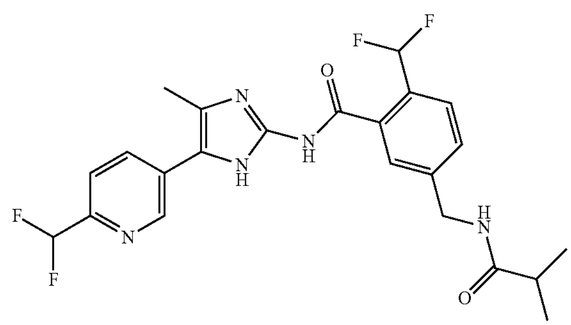 [SMILES: Cc1nc(NC(=O)c2cc(CNC(=O)C(C)C)ccc2C(F)F)[nH]c1-c1ccc(C(F)F)nc1] | 478 (M + 1) |
| 5 | BOP | 2-(Difluoromethyl)-5-[(2-methylpropanoylamino)methyl]-N-[4-methyl-5-[6-(trifluoromethyl)-3-pyridyl]-1H-imidazol-2-yl]benzamide | 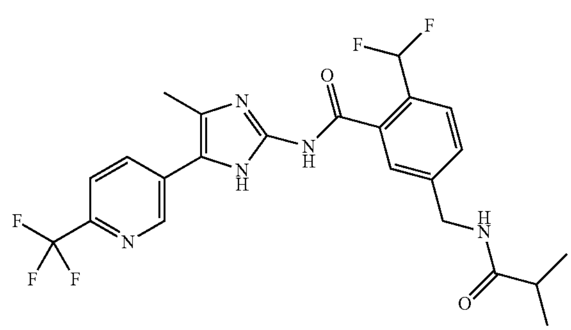 [SMILES: Cc1nc(NC(=O)c2cc(CNC(=O)C(C)C)ccc2C(F)F)[nH]c1-c1ccc(C(F)(F)F)nc1] | $^1$H NMR (399.83 MHz, d$_6$-DMSO) δ 12.16-12.14 (m, 1H), 11.87-11.85 (m, 1H), 9.02-8.99 (m, 1H), 8.34-8.31 (m, 1H), 8.20-8.17 (m, 1H), 7.87-7.85 (m, 1H), 7.71-7.66 (m, 2H), 7.51-7.47 (m, 2H), 4.34 (d, J = 5.9 Hz, 2H), 2.45-2.42 (m, 0H), 1.03 (d, J = 6.8 Hz, 6H). |

TABLE 11-continued

| Ex | Coupling Agent | Name | Structure | ES/MS (m/z) or ¹H NMR |
|---|---|---|---|---|
| 6 | BOP | 2-(Difluoromethyl)-N-[5-[4-(difluoromethyl)phenyl]-1H-imidazol-2-yl]-5-[(2-methylpropanoylamino)methyl]pyridine-3-carboxamide | 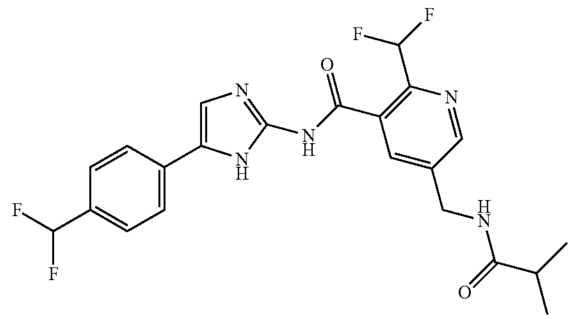 [SMILES: CC(C)C(=O)NCc1cnc(C(F)F)c(C(=O)Nc2ncc(-c3ccc(C(F)F)cc3)[nH]2)c1] | ¹H NMR (400.43 MHz, d₆-DMSO) δ 12.42-12.41 (m, 2H), 8.63-8.60 (m, 1H), 8.40-8.38 (m, 1H), 8.10-8.08 (m, 1H), 7.85-7.82 (m, 2H), 7.52-7.49 (m, 3H), 7.39-7.10 (m, 2H), 4.36-4.32 (m, 2H), 2.42-2.41 (m, 1H), 1.00 (d, J = 6.8 Hz, 6H). |
| 7 | BOP | 2-(Difluoromethyl)-5-[(2-methylpropanoylamino)methyl]-N-[5-[6-(trifluoromethyl)-3-pyridyl]-1H-imidazol-2-yl]benzamide | 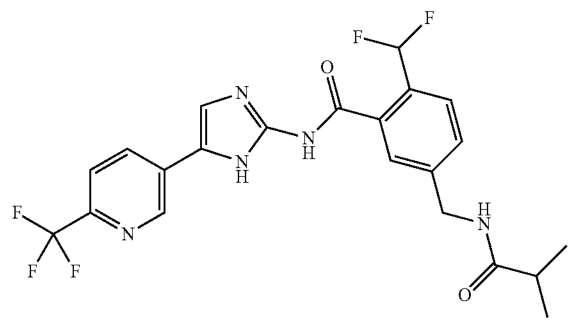 [SMILES: CC(C)C(=O)NCc1ccc(C(F)F)c(C(=O)Nc2ncc(-c3ccc(C(F)(F)F)nc3)[nH]2)c1] | ¹H NMR (400.43 MHz, d₆-DMSO) δ 12.28-12.27 (m, 2H), 8.63-8.60 (m, 1H), 8.40-8.38 (m, 1H), 8.11-8.08 (m, 1H), 7.85-7.82 (m, 2H), 7.52-7.49 (m, 3H), 7.39-7.10 (m, 1H), 5.71 (s, 1H), 4.36-4.32 (m, 2H), 2.43-2.41 (m, 1H), 1.00 (d, J = 6.8 Hz, 6H). |
| 8 | TBTU | N-[5-(4-Chlorophenyl)-1H-imidazol-2-yl]-2-(difluoromethyl)-5-[(2-methylpropanoylamino)methyl]pyridine-3-carboxamide | 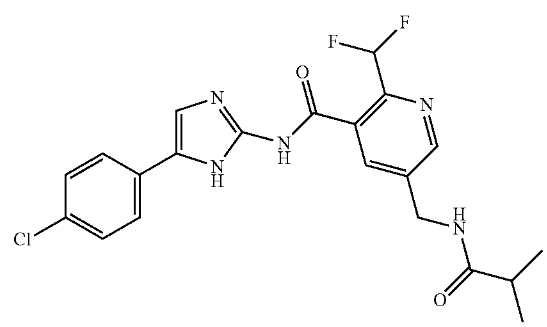 [SMILES: CC(C)C(=O)NCc1cnc(C(F)F)c(C(=O)Nc2ncc(-c3ccc(Cl)cc3)[nH]2)c1] | H1 NMR (399.80 MHz, d₆-DMSO) δ 12.25-12.22 (m, 2H), 8.63 (s, 1H), 8.40-8.35 (m, 1H), 8.06-8.02 (m, 1H), 7.74 (d, J = 8.5 Hz, 2H), 7.42-7.36 (m, 4H), 5.72 (s, 1H), 4.36 (d, J = 5.7 Hz, 2H), 2.45-2.40 (m, 1H), 1.02 (d, J = 6.8 Hz, 6H). |

TABLE 11-continued

| Ex | Coupling Agent | Name | Structure | ES/MS (m/z) or ¹H NMR |
|---|---|---|---|---|
| 9 | TBTU | N-[5-(3-Chlorophenyl)-4-methyl-1H-imidazol-2-yl]-2-(difluoromethyl)-5-[(2,2-dimethylpropanoylamino)methyl]pyridine-3-carboxamide | 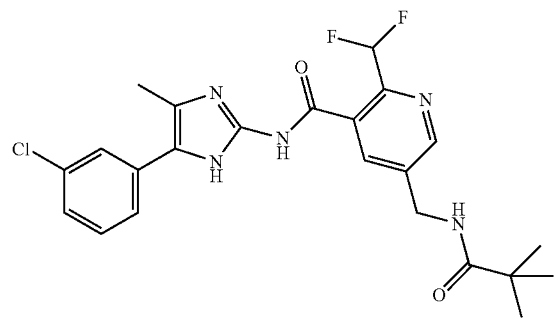 [SMILES: Cc1nc(NC(=O)c2cc(CNC(=O)C(C)(C)C)cnc2C(F)F)[nH]c1-c1cccc(Cl)c1] | ¹H NMR (399.80 MHz, d₆-DMSO) δ 12.12-12.09 (m, 2H), 8.57-8.54 (m, 1H), 8.17-8.15 (m, 1H), 8.02-8.01 (m, 1H), 7.56-7.55 (m, 1H), 7.52-7.50 (m, 1H), 7.40-7.39 (m, 1H), 7.25-7.24 (m, 1H), 4.33-4.28 (m, 2H), 2.35 (s, 3H), 1.06 (s, 9H). |
| 10 | TBTU | N-[5-(4-Chlorophenyl)-4-methyl-1H-imidazol-2-yl]-2-(difluoromethyl)-5-[(2,2-dimethylpropanoylamino)methyl]pyridine-3-carboxamide | 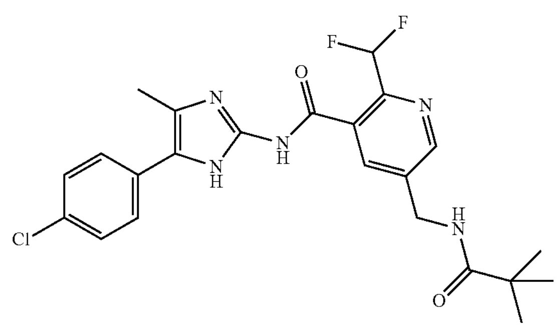 [SMILES: Cc1nc(NC(=O)c2cc(CNC(=O)C(C)(C)C)cnc2C(F)F)[nH]c1-c1ccc(Cl)cc1] | ¹H NMR (399.80 MHz, d₆-DMSO) δ 12.12-12.10 (m, 2H), 8.61 (d, J = 1.7 Hz, 1H), 8.40-8.36 (m, 1H), 8.08-8.04 (m, 1H), 7.59-7.57 (m, 2H), 7.43-7.41 (m, 2H), 7.38-7.36 (m, 1H), 4.35 (d, J = 5.7 Hz, 2H), 2.43-2.37 (m, 3H), 1.01 (d, J = 6.8 Hz, 6H). |
| 11 | TBTU | N-[5-(2,3-Dichlorophenyl)-4-methyl-1H-imidazol-2-yl]-2-(difluoromethyl)-5-[(2,2-dimethylpropanoylamino)methyl]pyridine-3-carboxamide | 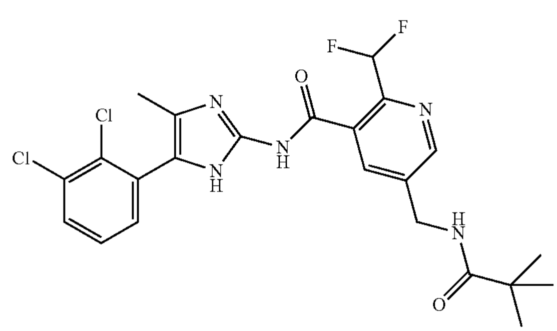 [SMILES: Cc1nc(NC(=O)c2cc(CNC(=O)C(C)(C)C)cnc2C(F)F)[nH]c1-c1cccc(Cl)c1Cl] | ¹H NMR (399.80 MHz, d₆-DMSO) δ 12.13-12.12 (m, 2H), 8.55 (d, J = 0.4 Hz, 1H), 8.16-8.12 (m, 1H), 8.04-8.02 (m, 1H), 7.61-7.59 (m, 1H), 7.36-7.32 (m, 2H), 7.29-7.27 (m, 1H), 4.31 (d, J = 5.6 Hz, 2H), 2.05 (s, 3H), 1.07 (s, 9H). |

TABLE 11-continued

| Ex | Coupling Agent | Name | Structure | ES/MS (m/z) or ¹H NMR |
|---|---|---|---|---|
| 12 | HATU | 2-(Difluoromethyl)-5-[(2-methylpropanoylamino)methyl]-N-[4-methyl-5-(p-tolyl)-1H-imidazol-2-yl]pyridine-3-carboxamide | 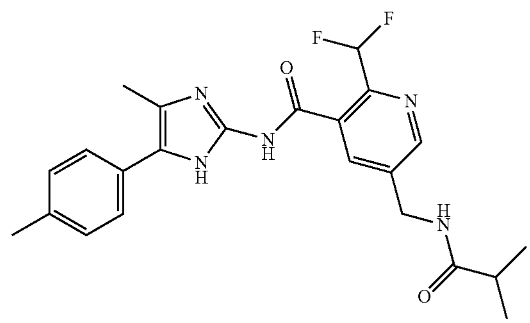 [SMILES: Cc1ccc(-c2[nH]c(NC(=O)c3cc(CNC(=O)C(C)C)cnc3C(F)F)nc2C)cc1] | 442 (M + 1) |
| 13 | HATU | 2-(Difluoromethyl)-N-[5-(4-fluorophenyl)-4-methyl-1H-imidazol-2-yl]-5-[(2-methylpropanoylamino)methyl]benzamide | 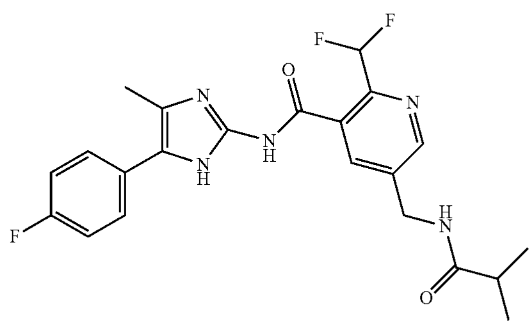 [SMILES: Cc1nc(NC(=O)c2cc(CNC(=O)C(C)C)cnc2C(F)F)[nH]c1-c1ccc(F)cc1] | 446 (M + 1) |
| 14 | TBTU | 2-(Difluoromethyl)-5-[(2,2-dimethylpropanoylamino)methyl]-N-[5-(3-fluoro-4-methyl-phenyl)-4-methyl-1H-imidazol-2-yl]pyridine-3-carboxamide | 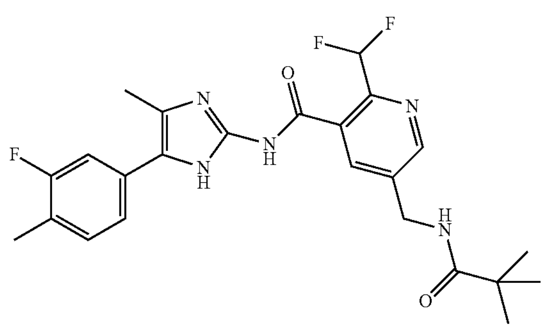 [SMILES: Cc1ccc(-c2[nH]c(NC(=O)c3cc(CNC(=O)C(C)(C)C)cnc3C(F)F)nc2C)cc1F] | 474 (M + 1) |
| 15 | TBTU | 2-(Difluoromethyl)-5-[(2,2-dimethylpropanoylamino)methyl]-N-[4-methyl-5-[2-methyl-4-(trifluoromethyl)phenyl]-1H-imidazol-2-yl]pyridine-3-carboxamide | 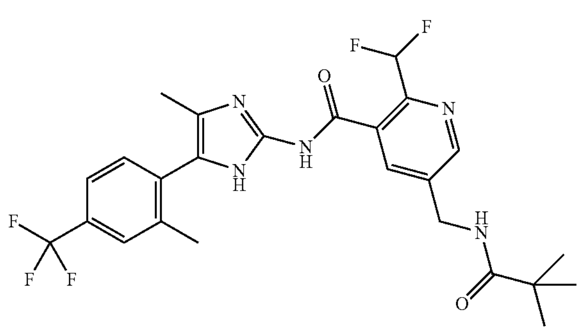 | 524 (M + 1) |

TABLE 11-continued

| Ex | Coupling Agent | Name | Structure | ES/MS (m/z) or ¹H NMR |
|---|---|---|---|---|
| 16 | TBTU | 2-(Difluoromethyl)-5-[(2,2-dimethylpropanoylamino)methyl]-N-[5-[2-fluoro-4-(trifluoromethyl)phenyl]-4-methyl-1H-imidazol-2-yl]pyridine-3-carboxamide | 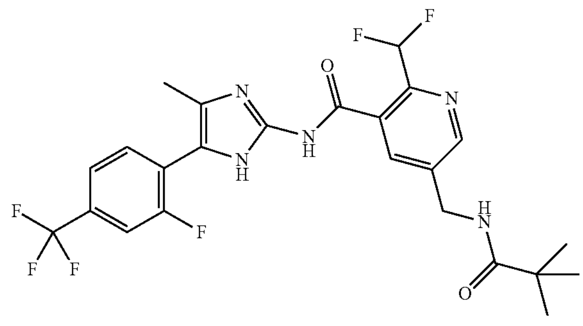 | 528 (M + 1) |
| 17 | TBTU | 2-(Difluoromethyl)-5-[(2,2-dimethylpropanoylamino)methyl]-N-[5-(3-fluorophenyl)-4-methyl-1H-imidazol-2-yl]pyridine-3-carboxamide | 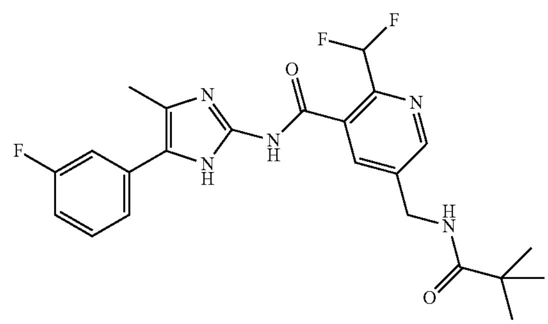 [SMILES: Cc1nc(NC(=O)c2cc(CNC(=O)C(C)(C)C)cnc2C(F)F)[nH]c1-c1cccc(F)c1] | 460 (M + 1) |
| 18 | TBTU | N-[5-(3-Chloro-4-methyl-phenyl)-4-methyl-1H-imidazol-2-yl]-2-(difluoromethyl)-5-[(2,2-dimethylpropanoylamino)methyl]pyridine-3-carboxamide | 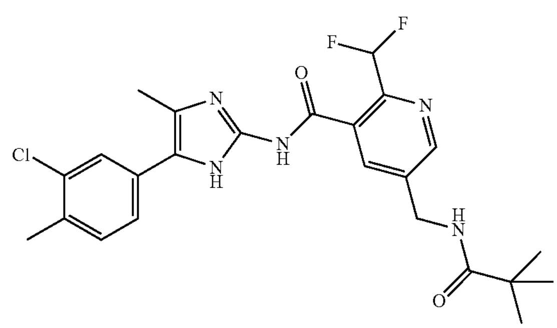 [SMILES: Cc1ccc(-c2[nH]c(NC(=O)c3cc(CNC(=O)C(C)(C)C)cnc3C(F)F)nc2C)cc1Cl] | 490/492 (M + 1 Cl³⁵/C³⁷) |
| 19 | TBTU | 2-(Difluoromethyl)-N-[5-(2,3-difluorophenyl)-4-methyl-1H-imidazol-2-yl]-5-[(2,2-dimethylpropanoylamino)methyl]pyridine-3-carboxamide | 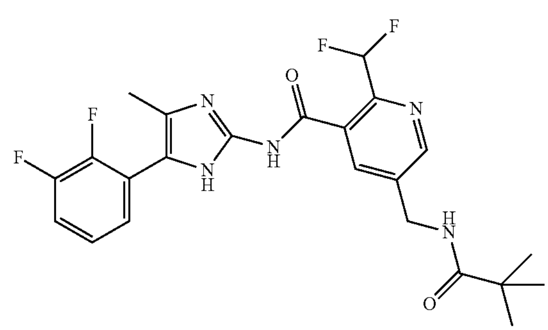 [SMILES: Cc1nc(NC(=O)c2cc(CNC(=O)C(C)(C)C)cnc2C(F)F)[nH]c1-c1cccc(F)c1F] | 478 (M + 1) |

TABLE 11-continued

| Ex | Coupling Agent | Name | Structure | ES/MS (m/z) or $^1$H NMR |
|---|---|---|---|---|
| 20 | TBTU | 2-(Difluoromethyl)-N-[5-(3,4-difluorophenyl)-4-methyl-1H-imidazol-2-yl]-5-[(2,2-dimethylpropanoylamino)methyl]pyridine-3-carboxamide | 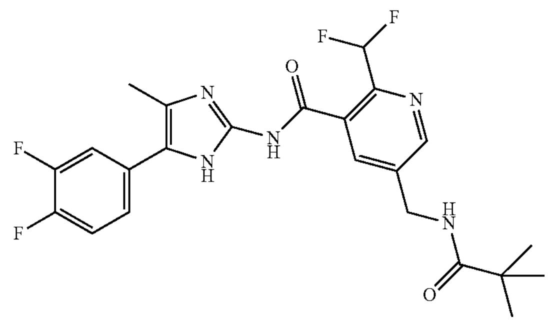 | 478 (M + 1) |
| 21 | TBTU | N-[5-(3,4-Dichlorophenyl)-4-methyl-1H-imidazol-2-yl]-2-(difluoromethyl)-5-[(2,2-dimethylpropanoylamino)methyl]pyridine-3-carboxamide | 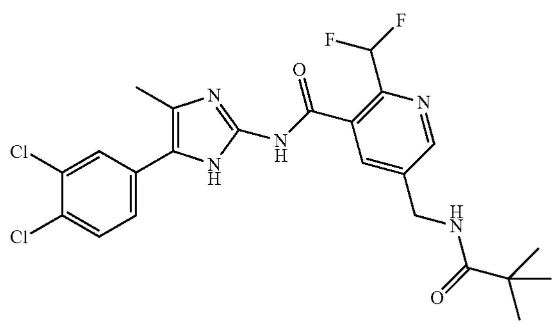 | 510/511/512/513 [M + 1 (2 Cl$^{35}$/C$^{37}$)] |
| 22 | TBTU | 2-(Difluoromethyl)-5-[(2,2-dimethylpropanoylamino)methyl]-N-[5-(4-fluoro-3-methyl-phenyl)-4-methyl-1H-imidazol-2-yl]pyridine-3-carboxamide | 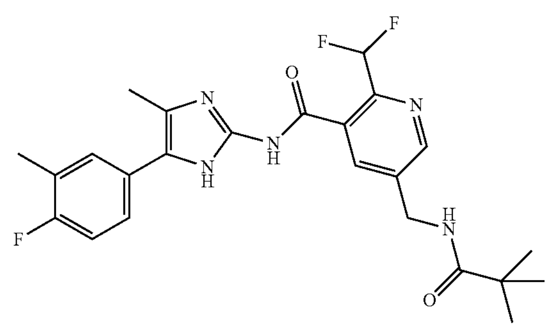 | 474 (M + 1) |
| 23 | TBTU | 2-(Difluoromethyl)-5-[(2,2-dimethylpropanoylamino)methyl]-N-[5-(2-fluoro-3-methyl-phenyl)-4-methyl-1H-imidazol-2-yl]pyridine-3-carboxamide | 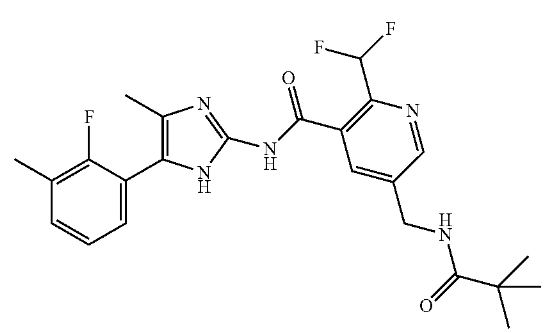 | 474 (M + 1) |

TABLE 11-continued

| Ex | Coupling Agent | Name | Structure | ES/MS (m/z) or $^1$H NMR |
|---|---|---|---|---|
| 24 | TBTU | N-[5-(2-Chloro-3-methyl-phenyl)-4-methyl-1H-imidazol-2-yl]-2-(difluoromethyl)-5-[(2,2-dimethylpropanoylamino)methyl]pyridine-3-carboxamide | 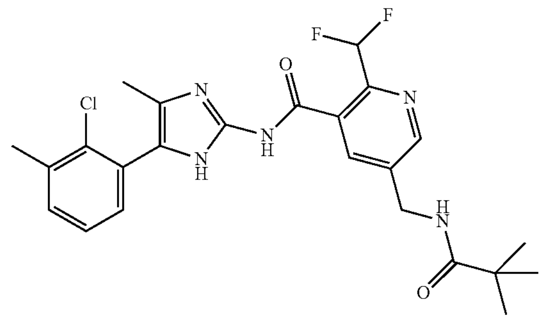 [SMILES: Cc1cccc(-c2[nH]c(NC(=O)c3cc(CNC(=O)C(C)(C)C)cnc3C(F)F)nc2C)c1Cl] | 490/492 (M + 1/ Cl$^{35}$/C$^{37}$) |
| 25 | TBTU | 2-(Difluoromethyl)-5-[(2,2-dimethylpropanoylamino)methyl]-N-[5-(2-fluorophenyl)-4-methyl-1H-imidazol-2-yl]pyridine-3-carboxamide | 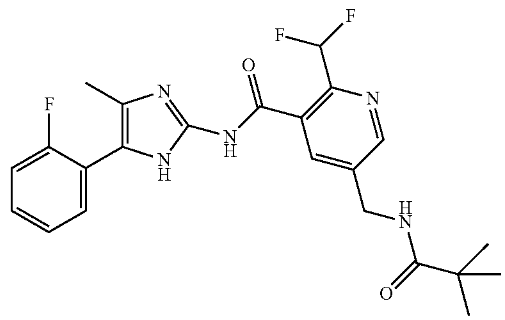 [SMILES: Cc1nc(NC(=O)c2cc(CNC(=O)C(C)(C)C)cnc2C(F)F)[nH]c1-c1ccccc1F] | 460 (M + 1) |

EXAMPLE 26

2-(Difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt

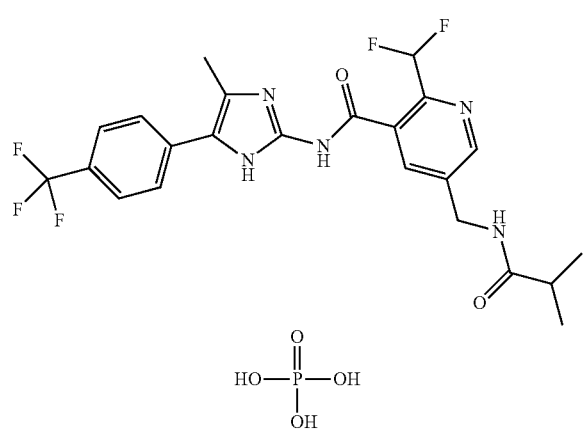

Charge a 250 mL round bottom flask with 5.58 g of 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide and 85% phosphoric acid (800 µL). To this mixture, add acetonitrile (40 mL) over the course of 20 minutes to produce a loose slurry. Stir the slurry at ambient temperature for 30 minutes. Collect the solids by vacuum filtration, and dry the solids under reduced pressure at 100° C. for several hours to provide the phosphate salt (5.6359 g, 92%).

XRD Spectrograph Analysis

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. Peak position variability of ±0.2 in 2θ will take into account potential variations without hindering the unequivocal identification of the indicated crystal form. The crystal form diffraction patterns, collected at ambient temperature and relative humidity, are adjusted based on NIST 675 standard peaks at 8.85 and 26.77 degrees 2-theta.

A sample of 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt prepared according to Example 26 is characterized by an XRD pattern using CuKa radiation and having diffraction peaks (2-theta values). Specifically the pattern contains a peak at 4.85 in combination with one or more of the peaks selected from the group consisting of 9.77, 16.68, 17.93, 19.15, 22.27 and 24.84 with a tolerance for the diffraction angles of 0.2 degrees. A listing of the major peaks in 2-theta is provided below in Table 12.

TABLE 12

| Peak | Angle (2-Theta °) | Intensity (%) |
|---|---|---|
| 1 | 4.85 | 96 |
| 2 | 9.77 | 28 |
| 3 | 10.63 | 36 |

TABLE 12-continued

| Peak | Angle (2-Theta °) | Intensity (%) |
|---|---|---|
| 4 | 11.00 | 57 |
| 5 | 12.22 | 47 |
| 6 | 12.67 | 44 |
| 7 | 16.68 | 25 |
| 8 | 17.93 | 56 |
| 9 | 18.24 | 29 |
| 10 | 19.15 | 41 |
| 11 | 20.37 | 68 |
| 12 | 22.27 | 100 |
| 13 | 23.51 | 46 |
| 14 | 24.84 | 54 |

EXAMPLE 26

Alternate Procedure

Add 2-(Difluoromethyl)-5-{[(2-methylpropanoyl)amino]methyl}-N-{4-methyl-5-[4-(trifluoromethyl)phenyl]-1H-imidazol-2-yl}pyridine-3-carboxamide (250 g, 0.505 mol, 1 eq) to ACN, (5 L). Add a solution of 85% $H_3PO_4$, (110.7 g, 0.960 mol $H_3PO_4$, 1.90 eq) in deionized water, (1 L) to the mixture. Heat the reaction mixture to 60-70° C., and then filter through a 1.2 μm filter capsule into a 15 L reactor. Heat the resulting slurry to 55-65° C. and stirat ambient temperature overnight. Thereafter cool the slurry to 5° C. and stir for about 2 hours while maintaining the reaction temperature at 5° C. Collect the solids, and rinse the solids with cold ACN (0-10° C., 2×475 mL) and cold deionized water (0-10° C., 2×475 mL). Return the wet solids (354 g) to the reactor, and slurry the solids with deionized water (2.5 L) at ambient temperature for 2 h. Collect the solids by filtration, and rinse the solids with the filtrate (3 times) followed by deionized water (1.25 L). Dry the off-white solids under reduced pressure at 110° C. with a stream of nitrogen to give the title compound as a pale yellow solid (237 g, 79% yield). Analysis for $C_{23}H_{22}F_5N_5O_2H_2PO_4$: calcd: C, 46.55; H, 4.25; F, 16.01; N, 11.80. found: C, 46.63; H, 4.22; F, 16.30; N, 11.91. $^1$H-NMR (400 MHz, $d_6$-DMSO) δ 8.66 (d, J=1.8 Hz, 1H), 8.45 (t, J=5.8 Hz, 1H), 8.08 (s, 1H), 7.76 (dd, J=33.3 Hz, 4H), 7.36 (t, J=54.3 Hz, 1H), 4.40 (d, J=5.8 Hz, 2H), 2.45 (s, 3H), 2.45 (m, J=6.9 Hz, 1H), 1.04 (d, J=6.9 Hz, 6H).

EXAMPLE 27

5-(Acetamidomethyl)-2-(difluoromethyl)-N-[4-methyl-5-[4-(trifluoromethyl)phenyl]-1H-imidazol-2-yl]pyridine-3-carboxamide

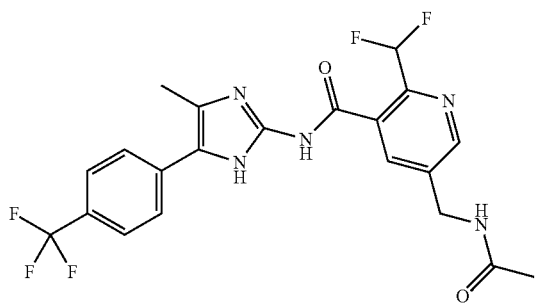 [SMILES: CC(=O)NCc1cnc(C(F)F)c(C(=O)Nc2nc(C)c(-c3ccc(C(F)(F)F)cc3)[nH]2)c1]

Dissolve 5-(aminomethyl)-2-(difluoromethyl)-N-[4-methyl-5-[4-(trifluoromethyl)phenyl]-1H-imidazol-2-yl]pyridine-3-carboxamide (0.047 g, 0.110 mmol) in DCM (3 mL). Add triethylamine (0.038 mL, 0.276 mmol) followed by acetyl chloride (9.830 μL, 0.138 mmol), and stir overnight. Pour the reaction into saturated aqueous $NH_4Cl$ (15 mL) solution, and extract with EtOAc (2×10 mL). Combine the organic extracts; dry the organic extracts over sodium sulfate; filter; collect the filtrate; and concentrate the filtrate under reduced pressure to dryness to give the title compound (0.039 g, 75% yield) as a light yellow solid. LCMS (m/z) 468 (M+1).

EXAMPLE 28

2-(Difluoromethyl)-N-[4-methyl-5-[4-(trifluoromethyl)phenyl]-1H-imidazol-2-yl]-5-[(propanoylamino)methyl]pyridine-3-carboxamide

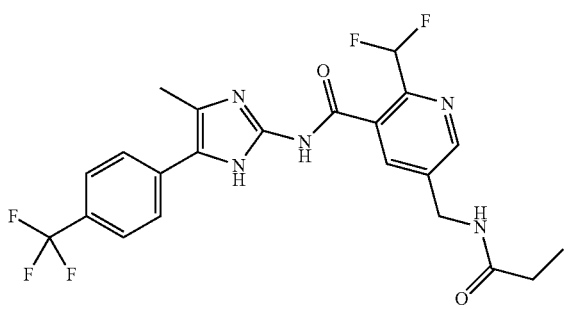 [SMILES: CCC(=O)NCc1cnc(C(F)F)c(C(=O)Nc2nc(C)c(-c3ccc(C(F)(F)F)cc3)[nH]2)c1]

Prepare essentially by the method of Example 27 with the appropriate amine and acid chloride. ES/MS (m/z) 482 (M+1)

Biological Assays

Human mPGES-1 Enzyme Inhibition Assay

Human mPGES-1 (Invitrogen™ (Cat #97002RG, clone ID 6374722)) is subcloned into pcDNA3.1 and transiently expressed in 293E cells. Microsomes are prepared from cell pellets based on published methods (Oullet et al., Purification and characterization of recombinant microsomal prostaglandin E synthase-1, Protein Expression and Purification, 26 pp 489-495 (2002); and Thoren et al., Human Microsomal Prostanglandin E Synthase-1, J. Biol. Chem. 278(25) pp 22199-22209 (2003)). Briefly, pellets are brought up in homogenization buffer (15 mM Tris-HCl, pH 8.0; 0.25 M sucrose; 0.1 mM EDTA; 1 mM glutathione) and sonicated 5×30 seconds on ice. Homogenate is centrifuged at 5000×g for 10 minutes at 4° C. The supernatant fraction is decanted; loaded into Beckman Quick-Seal® tubes; and centrifuged at 150,000×g for 90 minutes at 4° C. The supernatant fraction is discarded by decantation; and the pellets are resuspended in assay buffer (10 mM sodium phosphate (pH 7.0), 10% glycerol, and 2.5 mM glutathione. Complete Protease Inhibitor Cocktail (Roche)). Protein concentration is determined using the Pierce Coomassie Plus™ reagent.

For the enzyme assay, the microsomes are diluted into assay buffer and 7 μL/well is added to 384 well plates. Compound dilution plates (Nunc Cat #249944) are generated on a Multimek™, and 1 μL/well is added to the assay plates. Prostaglandin $H_2$ ($PGH_2$) is diluted into assay buffer immediately before use and 7 μL/well is added. Final concentrations are 4.4 μg/mL microsomes and 1.69 μM $PGH_2$. After a 2.5 minute incubation at room temperature, 2.5 μL/well of 1 mg/mL of $snCl_2$ in 0.5 N HCl is added to stop the reaction. Five μL of the reaction is transferred to a 384 well plate and acetonitrile (45 μL) containing deuterated $PGE_2$ as an internal standard is added with a Multidrop; and the plates are stored at −20° C. The plates are analyzed for $PGE_2$ using standard LC/MS analysis (Biocius Lifesciences (Wakefield, Mass. 01880). The data is used to calculate the $IC_{50}$ (μM). The results indicate that the Example 1 (2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide) inhibits human mPGES-1 with an $IC_{50}$ (μM) value of 0.000944±0.00059 μM (mean±standard deviation; n=10/22). The exemplified compounds exhibit an $IC_{50}$ of less than 100 nM. Thus the exemplified compounds are a potent inhibitors of the mPGES-1 enzyme in an isolated enzyme preparation.

Cell Based Assay for Measuring Eicosanoid Selectivity

Human epithelial lung carcinoma cell line A549 is obtained from ATCC (CCL-185) and is maintained in Kaighn's F12 ("F12K")+10% fetal bovine serum, (FBS) (plating medium), and 5% $CO_2$. The cells are passaged at 1:3 twice a week.

For this assay, cells are released from flasks by washing once with phosphate buffered saline (PBS), then once with Trypsin/EDTA. After 3-5 minutes at 37° C., the cells are suspended in 10 mL of plating medium, and centrifuged at 2,000 rpm at 25° C. for 5 minutes. The supernatant is aspirated, and the cell pellet is resuspended in 10 mL F12K. Cell number is determined by counting an aliquot of cells, which has been diluted in PBS and Trypan blue on a hemocytometer. Cells are plated at 40,000/well in 96 well Falcon plates 24 hours prior to treatment. Compounds are diluted in DMSO to 100× of the final concentration in Screen Mates tubes. The medium is removed from the cells, and fresh medium (90 μL/well) is added to the cells. The compounds are added at 1 μL/well, n=2, to give seven concentrations each. Cells are pretreated for 30 minutes at 37° C., 5% $CO_2$. Prostaglandin $E_2$ production was induced by the addition of recombinant human interleukin 1β (rhIL-1β) diluted in plating medium to 10× final. A 10 μL/well aliquot is added to give a final rhIL-1β concentration of 0.1-0.2 ng/mL. The treatment period is approximately 18 hours. Conditioned medium is removed to v-bottom polypropylene plates. Serum-free F12K is added to the cells (50 μL/well) along with CellTiter96 reagent (Promega™) (10 μL/well). The plates are incubated at room temperature for 30-45 minutes, and then read on a plate reader at A490 to determine viability. A control well receives 10 μL/well 10% triton X-100 to serve as a toxic control.

The conditioned medium is assayed for levels of $PGE_2$ and $PGI_2$ by specific enzyme immune-assays (ETAs) according to the manufacturer's protocols (Cayman) Briefly, conditioned medium (1 μL) is added to each well of a 96 well plate coated with a capture antibody and containing ETA buffer (49 μL) supplied by the manufacturer. The tracer is diluted with the ETA buffer, and added (50 μL/well). The detection antibody is diluted with the ETA buffer and added (50 μL/well). The plate is covered with adhesive sealing film, and is incubated for 1 hour at room temperature on an orbital shaker at 100 rpm. The wash buffer is diluted into Millipore purified water, and the plate is washed 5×350 μL/well using a plate washer. The substrate (Ellman's reagent) is diluted in Millipore purified water and added (200 μL/well). After approximately 45 minutes at room temperature on an orbital shaker at 100 rpm, the plates are read at A412 on a plate reader. A standard curve of $PGE_2$ is used to calibrate the unknowns. Example 1 (2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide) inhibits $PGE_2$ formation with an $IC_{50}$ of 0.0121±0.0061 μM (mean±standard deviation; n=4) without affecting the synthesis of other prostanoids. Thus the exemplified compound is shown to selectively inhibit $PGE_2$ synthesis without inhibiting the synthesis of other prostanoids.

Human Whole Blood Assay

Blood is collected from normal volunteer donors into sodium heparin vacutainer tubes. Donors have not taken NSAIDs, aspirin, Celebrex, or glucocorticoids within two weeks of the donation. All tubes/donor are pooled into 250 mL Corning conical centrifuge tubes and 436.5 μL/well is distributed into deep well polypropylene plates. Compounds are diluted in DMSO to 100× final and 4.5 μL/well in duplicate or triplicate is added to give 7 point curves. The blood is pretreated at 37° C., 5% $CO_2$, in a humidified atmosphere, loosely covered with a silicone cap mat, for 30 minutes after which 9 μL/well of a solution of 5 mg/mL of lipopolysaccharide (LPS) (Sigma 0111:B4) in 1 mg/mL bovine serum albumin (BSA)/PBS is added to give a final LPS concentration of 100 μg/mL. The plates are incubated for 20-24 hours, loosely covered, at 37° C., 5% $CO_2$, in a humidified atmosphere, on an orbital shaker at approximately 100 rpm. The plates are tightly sealed with silicone cap mats and are chilled on ice for approximately 1 hour. Then the plates are centrifuged at 1800×g, 10 minutes, 4° C., in an Eppendorf 5810R centrifuge. Plasma is removed from the cell layer using the Rainin L200 with sterile filtered tips and transferred to v-bottom polypropylene plates. One hundred microliters is quantitatively transferred to Costar cluster tubes blocks and 400 μL/well of the methanol stop reagent and internal standards, d-4$PGE_2$, d-4$PGF_{2\alpha}$, and d-4$TX_{2\beta}$ are added. Samples are vortexed for 5 minutes and are placed at −20° C. for at least one hour. Samples are centrifuged for 10 minutes at 4000 rpm in an Eppendorf 5810R. Solid phase extraction is performed using Waters HLB 30 mg/bed 96 well plates on a vacuum manifold: 1) the matrix is washed with methanol (1 mL), followed by 0.1% formic acid in water (1 mL); 2) 400 μL sample is applied along with 0.1% formic acid in water (900 mL) and allowed to bind for 5 minutes; 3) the matrix is washed with 0.1% formic acid in water (600 mL), followed by 80/20 water/methanol (600 mL); 4) the products are eluted with 2-500 μL volumes of ethyl acetate; 5) the samples are dried under nitrogen and reconstituted in of 75/25 water/acetonitrile with 0.1% formic acid (50 mL). The products were analyzed by LC/MS/MS. The compound 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide (Example 1) selectively inhibits $PGE_2$ production with an $IC_{50}$ of 0.012±0.0.008 μM (geometric mean±standard deviation; n=11) without inhibiting $PGF_{2\alpha}$ and $TXB_2$ production.

Monoiodoacetate (MIA) In Vivo Model

Male Dunkin Hartley guinea pigs weighing approximately 200-250 grams at the time of MIA injection are used to measure pain in the MIA model. The guinea pigs are group housed in a child's wading pool and maintained in a constant temperature and on a 12 hour light/12 hour dark cycle. On the day before study, the guinea pigs are moved to standard caging with 2 animals per cage. Animals have free access to food and water at all times except during data collection. All experiments are carried out according to protocols approved by the Eli Lilly Institutional Animal Care and Use Committees.

In the standard MIA model the right knees of each guinea pig are injected with MIA (0.3 mg) in saline (50 nl) and the left knees with saline (50 μl). Pain is measured at 9 days after MIA injection using incapacitance testing. Incapacitance testing measures the difference in hind paw weight bearing between the MIA and saline injected knees, and each value represents the average of 3 separate measurements each measured over 1 second.

For this study, guinea pigs, are dosed with either vehicle (10% Cremophor® EL (CAS 61791-12-6) in saline) or Example 1 (10 or 50 mg/kg). A fourth group of guinea pigs are also dosed with the nonsteroidal anti-inflammatory drug diclofenac (vehicle saline, 30 mg/kg), which acts as a positive control for the study, as it has previously shown efficacy in the model. All dosing is subcutaneous at a dose volume of 5 ml/kg and group size is n=6. Dose group is randomly assigned to each animal and dosing is staggered by 10 minutes for each guinea pig. Four hours post-dose, pain is measured using incapacitance testing. Results are reported in Table 13 as the mean difference in weight bearing between saline and MIA injected knees and statistical comparisons are made between vehicle treated and compound treated animals to assess the effect of the compound of Example 1 on knee pain in the model.

TABLE 13

| Compound | Mean Difference in Hind Paw Weight Bearing (Saline knee-MIA knee)(g) | Mean % Reduction of Pain Compared to Vehicle |
|---|---|---|
| Vehicle | 44.29 ± 0.69 | |
| Example 1, 10 mg/kg | 37.53 ± 0.87 | 15 |
| Example 1, 50 mg/kg | 28.44 ± 0.66 | 36 |
| Diclofenac, 30 mg/kg | 34.65 ± 1.14 | 22 |

Mean ± SEM;
SEM = standard error of the mean

Data is evaluated by one way analysis of variance; $p<0.05$ by Dunnett's test for comparison to vehicle and a Bonferroni adjustment is used for comparison between groups.

Both doses of the compound of Example 1 and diclofenac significantly reduce pain verses vehicle with the 50 mg/kg group of Example 1 being significantly different from the 10 mg/kg group and the diclofenac group.

The exemplified compounds of the present invention can be readily formulated into pharmaceutical compositions in accordance with accepted practice such as found in Remington's Pharmaceutical Sciences, Gennaro, Ed., Mack Publishing Co. Easton Pa. 1990.

Preferred pharmaceutical compositions can be formulated as a tablet or capsule for oral administration. The tablet or capsule includes a compound of the present invention in an effective amount. The pharmaceutical composition is administered to a patient in amounts effective to treat osteoarthritis pain. An appropriate amount or dose effective to treat a patient can be determined by a health care provider.

What is claimed is:

1. A compound of a formula below:

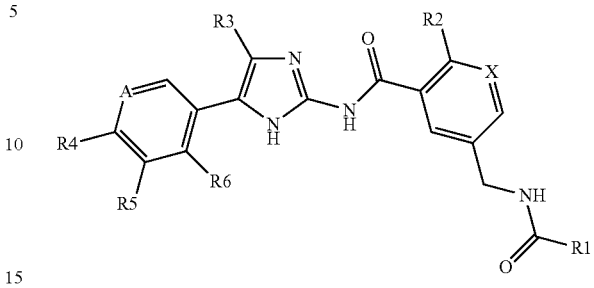

wherein

R1 is selected from: —$C_{1-4}$alkyl;

R2 is Cl or —$CHF_2$;

R3 is H or —$CH_3$;

R4 is selected from: H, F, Cl, —$CH_3$, —$CHF_2$, and —$CF_3$;

R5 is selected from: H, F, Cl, and —$CH_3$;

R6 is selected from: H, F, Cl, and —$CH_3$; and one of X and A is N and the other one of X and A is CH;

provided that when A is N, R4 is not F or Cl and when X is N, R2 is not Cl;

or a pharmaceutically acceptable salt thereof.

2. A compound according to claim 1 wherein R1 is —CH$(CH_3)_2$ or —$C(CH_3)_3$ or a pharmaceutically acceptable salt thereof.

3. A compound according to claim 1 wherein R1 is —CH$(CH_3)_2$, or a pharmaceutically acceptable salt thereof.

4. A compound according to claim 1 wherein R3 is —$CH_3$, or a pharmaceutically acceptable salt thereof.

5. A compound according to claim 1 wherein R5 is selected from: H, F, and Cl, or a pharmaceutically acceptable salt thereof.

6. A compound according to claim 1 wherein R5 is H, or a pharmaceutically acceptable salt thereof.

7. A compound according to claim 1 wherein R6 is H or a pharmaceutically acceptable salt thereof.

8. A compound according to claim 1 wherein R4 is selected from: H, —$CH_3$, —$CHF_2$, and —$CF_3$, or a pharmaceutically acceptable salt thereof.

9. A compound according to claim 1 wherein A is N, or a pharmaceutically acceptable salt thereof.

10. A compound according to claim 1 wherein R4 is selected from: F, Cl, —$CHF_2$, and —$CF_3$, or a pharmaceutically acceptable salt thereof.

11. A compound according to claim 1 wherein R4 is selected from: Cl, —$CHF_2$, and —$CF_3$, or a pharmaceutically acceptable salt thereof.

12. A compound according to claim 1 wherein R4 is —$CF_3$, or a pharmaceutically acceptable salt thereof.

13. A compound according to claim 1 wherein R2 is Cl, or a pharmaceutically acceptable salt thereof.

14. A compound according to claim 1 wherein R2 is —$CHF_2$, or a pharmaceutically acceptable salt thereof.

15. A compound according to claim 1 wherein X is N, or a pharmaceutically acceptable salt thereof.

16. A compound which is:

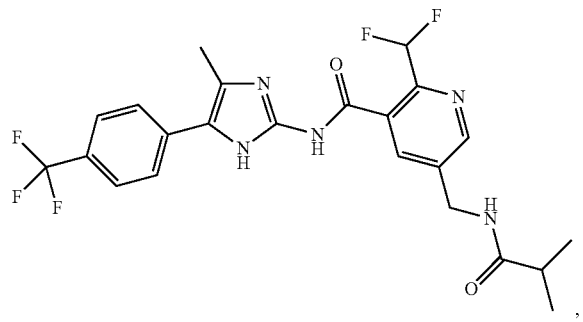 [SMILES: Cc1nc(NC(=O)c2cc(CNC(=O)C(C)C)cnc2C(F)F)[nH]c1-c1ccc(C(F)(F)F)cc1]

or a pharmaceutically acceptable salt thereof.

17. A compound according to claim 16 wherein the salt is a hydrogen phosphate salt.

18. A compound which is 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt in crystalline form characterized by an X-ray powder diffraction pattern obtained from a CuKα source ($\lambda=1.54056$ A), which comprises peaks at:

a) 4.85°, 11.00°, 17.93°, 20.37°, 22.27°, and 24.85°+/−0.2° in 2θ; or
b) 4.85°, 11.00°, 12.22°, 12.67°, 17.93°, 20.37°, 22.27°, 23.51°, and 24.85°+/−0.2° in 2θ.

19. A composition comprising 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide-hydrogen phosphate salt, of which greater than 80% by weight is in the crystalline form of claim 18.

20. A pharmaceutical composition comprising 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt in crystalline form according to claim 18 and at least one of a pharmaceutically acceptable carrier, diluent, or excipient.

21. A pharmaceutical composition comprising substantially pure 2-(difluoromethyl)-5-{[(2-methylpropanoyl)amino]methyl}-N-{4-methyl-5-[4-(trifluoromethyl)phenyl]-1H-imidazol-2-yl}pyridine-3-carboxamide.hydrogen phosphate salt in crystalline form according to claim 18 and at least one of a pharmaceutically acceptable carrier, diluent, or excipient.

22. A method of treating a patient in need of treatment for pain associated with arthritis, said method comprising administering to the patient an effective amount of a compound, or a pharmaceutically acceptable salt thereof, according to claim 1.

* * * * *